(12) United States Patent
Wakamiya et al.

(10) Patent No.: US 8,609,606 B2
(45) Date of Patent: Dec. 17, 2013

(54) POLYPEPTIDE ACTING TO ENHANCE ISCHEMIC DISEASES

(75) Inventors: Nobutaka Wakamiya, Asahikawa (JP); Katsuki Otani, Asahikawa (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 13/582,495

(22) PCT Filed: Mar. 4, 2011

(86) PCT No.: PCT/JP2011/001285
§ 371 (c)(1),
(2), (4) Date: Nov. 30, 2012

(87) PCT Pub. No.: WO2011/108281
PCT Pub. Date: Sep. 9, 2011

(65) Prior Publication Data
US 2013/0065817 A1    Mar. 14, 2013

(30) Foreign Application Priority Data
Mar. 4, 2010   (JP) ................. 2010-047335

(51) Int. Cl.
*A61K 38/16*    (2006.01)
(52) U.S. Cl.
USPC ......................... 514/1.9; 514/21.2
(58) Field of Classification Search
None
See application file for complete search history.

(56) References Cited

U.S. PATENT DOCUMENTS

| 7,189,809 B2 * | 3/2007 | Wakamiya | 530/350 |
| 7,612,174 B2 * | 11/2009 | Wakamiya | 530/350 |
| 7,612,175 B2 * | 11/2009 | Wakamiya | 530/350 |
| 8,410,253 B2 * | 4/2013 | Wakamiya | 530/387.9 |

FOREIGN PATENT DOCUMENTS

| JP | 10-179169 A | 7/1998 |
| JP | 11-206377 A | 8/1999 |
| JP | 2001-340089 A | 12/2001 |
| WO | WO-00/11161 A1 | 3/2000 |
| WO | WO-00/68380 A2 | 11/2000 |
| WO | WO-01/59107 A1 | 8/2001 |
| WO | WO-2004/024925 A2 | 3/2004 |

OTHER PUBLICATIONS

Search results for "Ischemia" from Merck Manual, p. 1. Accessed Apr. 17, 2013.*
Acute Mesenteric Ischemia from Merck Manual, pp. 1-2. Accessed Apr. 17, 2013.*
Definition of Arteriosclerosis from Merck Manual, p. 1. Accessed Apr. 17, 2013.*
Atherosclerosis from Merck manual, pp. 1-5. Accessed Apr. 17, 2013.*
Nonatheromatous Arteriosclerosis from Merck Manual, p. 1. Accessed Apr. 17, 2013.*
International Search Report of PCT/JP2011/001285 dated Mar. 29, 2011.
Ohtani et al., "The membrane-type collectin -CL-P1 is a scavenger receptor on vascular endothelial cells", J. Biol. Chem., 276(47):44222-44228 (2001).
Sumiya, et. al., "Molecular basis of opsonic defect in immunodeficient children," Lancet, 337: 1569-1570 (Jun. 1991).
Super, et. al., "Association of Low Levels of Mannan binding Protein with a Common Defect of Opsonisation," Lancet, 2:1236-1239 (Nov. 1989).
Suzuki et al., "Cloning and Sequencing of a cDNA Coding for Bovine Conglutinin," Biochem Biophys Res Commun, 191/2, 335-342 (1993).
Suzuki, et al., "Characterization of Recombinant Bovine Conglutinin Expressed in a Mammalian Cell", Biochem. Biophys. Res. Commun., 238:856-863 (1997).
Wakamiya, N. et. al., "The Mannose Binding Protein and Congulutinin in Bovine Serum Have a Antiviral Activity Against Influenza Virus," Glycoconjugate Journal, 8:235 (1991).
Wakamiya, N. et. al., "Isolation and Characterization of Conglutinin as an Influenza A Virus Inhibitor," Biochem. Biophys. Res. Comm., 187:1270-1278 (Sep. 1992).
Extended European Search Report for 11750394.6 dated Jul. 4, 2013.

* cited by examiner

*Primary Examiner* — Julie Ha
(74) *Attorney, Agent, or Firm* — Marshall, Gerstein & Borun LLP

(57) ABSTRACT

Disclosed is a polypeptide of use in the development of reagents or medicines favourable to application for prevention or treatment of ischemic disorders such as conditions caused by ateriosclerosis. The polypeptide has at least one part containing an amino acid of sequence ID 1, and also enhances expression levels of the amino acid in mammalian blood vessels removed from ischemic conditions by means of blood reperfusion.

2 Claims, 11 Drawing Sheets

```
human MBP              GSPGEKQKGDPKSPDG----DSSLRASERKALQTEMARIKKWLTFSLG-KQVGNKFFLTNGEIMTFEK
human SP-A             CEACERCF---PGLPA----HLDEELQATLHDFRHQILQTRGALSLQSIMTVGEKVFSSNGQSITFDA
human SP-D             GIPGDKGAKGESGLPDVASLRQQVEALQGQVQHLQAAFSQYKKVELFPNG-QSVGEKIFKTAGFVKPFTE
human novel collectin  GPPGPGF---SGAVVPLAFQNEPTPAPEDNGC-------------------PHWKNFTDKCYYFSVEKEIEFD     280

VEALQVKFQASVATPRNAAENGAIQNLI----KEEAFLDITEKTEGQFVDITGNRLTYTNWNEGFNN------
                       IQEAQARAGGRIAVPRNFEENEAIASFVKKYNTYAYVGLTEGPSPGDFRYSDGTPVNYTNWYRGERAG-----
                       AQLLQTQAGGQLASPRSAANAALQQLVMAKNFAAFLSMIDSKTEGKFTYPTEESLVMSNAPGEPNDKT-----
                       AKIFQEDKSSHIVFINTREEQQWMKKQMWG-RESHWIGLTDSERENEWKWLDGTSPDYKNWKAGQEDNWG     350

---AGSDEDQVLILKNGQWNDVPCSTSHLAVCEFPI*-------
                       -R---KEQCVEMYTDGQWNDRNCLYSRLTHCDF*----------
                       --DGGSEDQVEIFTNGKWNDRACGEKRLVVCEF*----------
                       HGHCPGEDCAGIIYAGQWNDFQCEDVNNFICEKDRETVLSSAL*
```

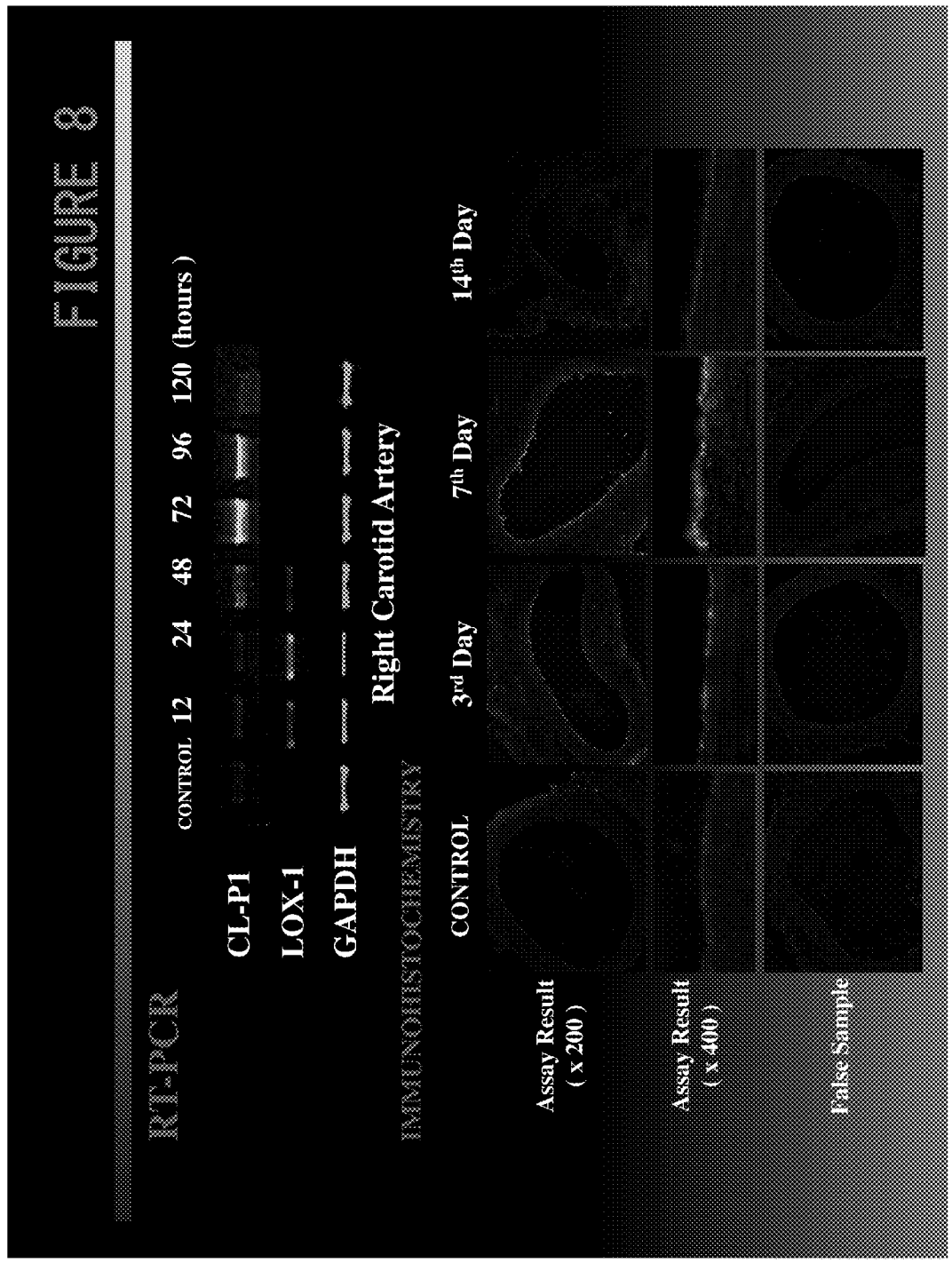

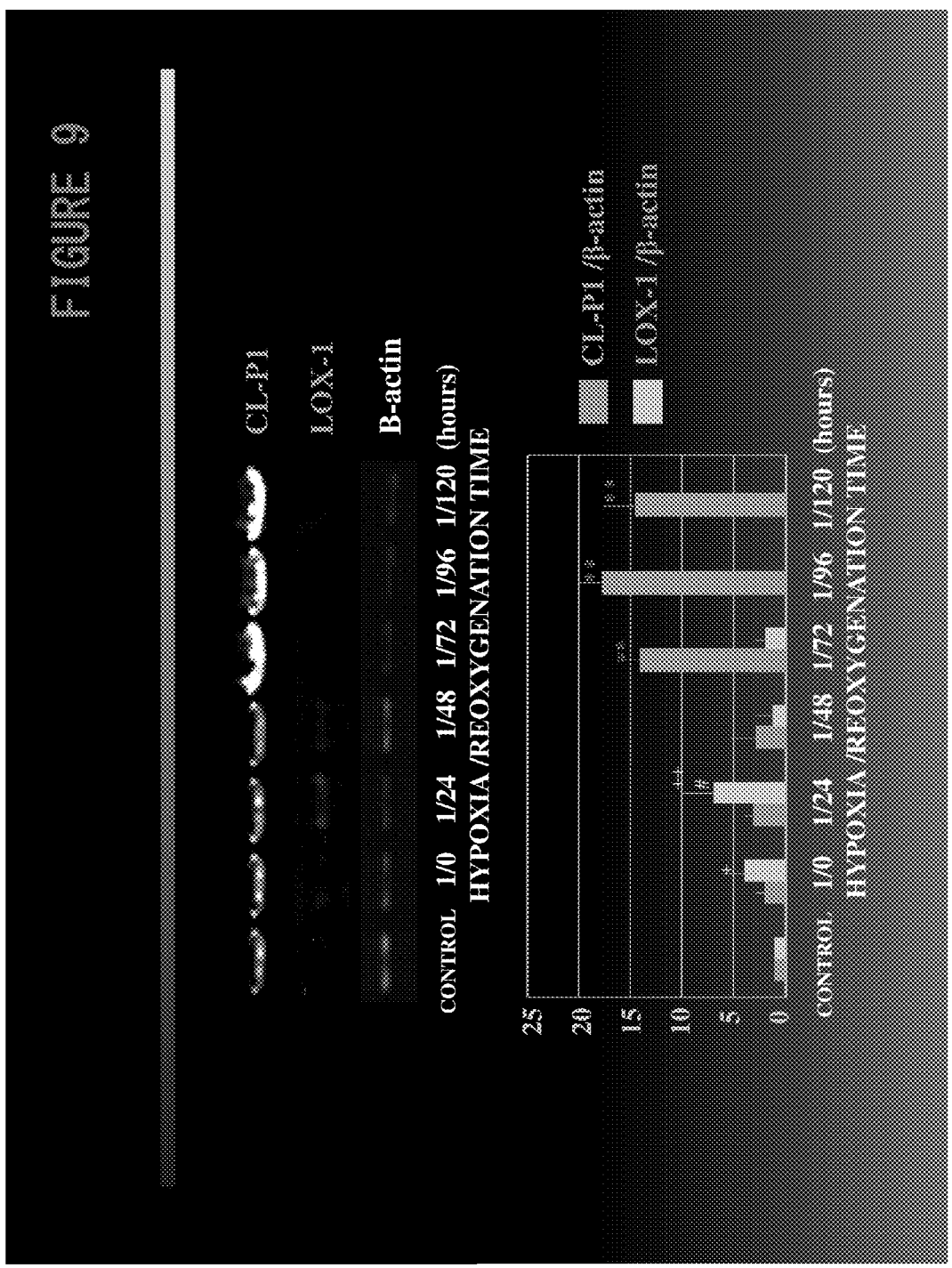

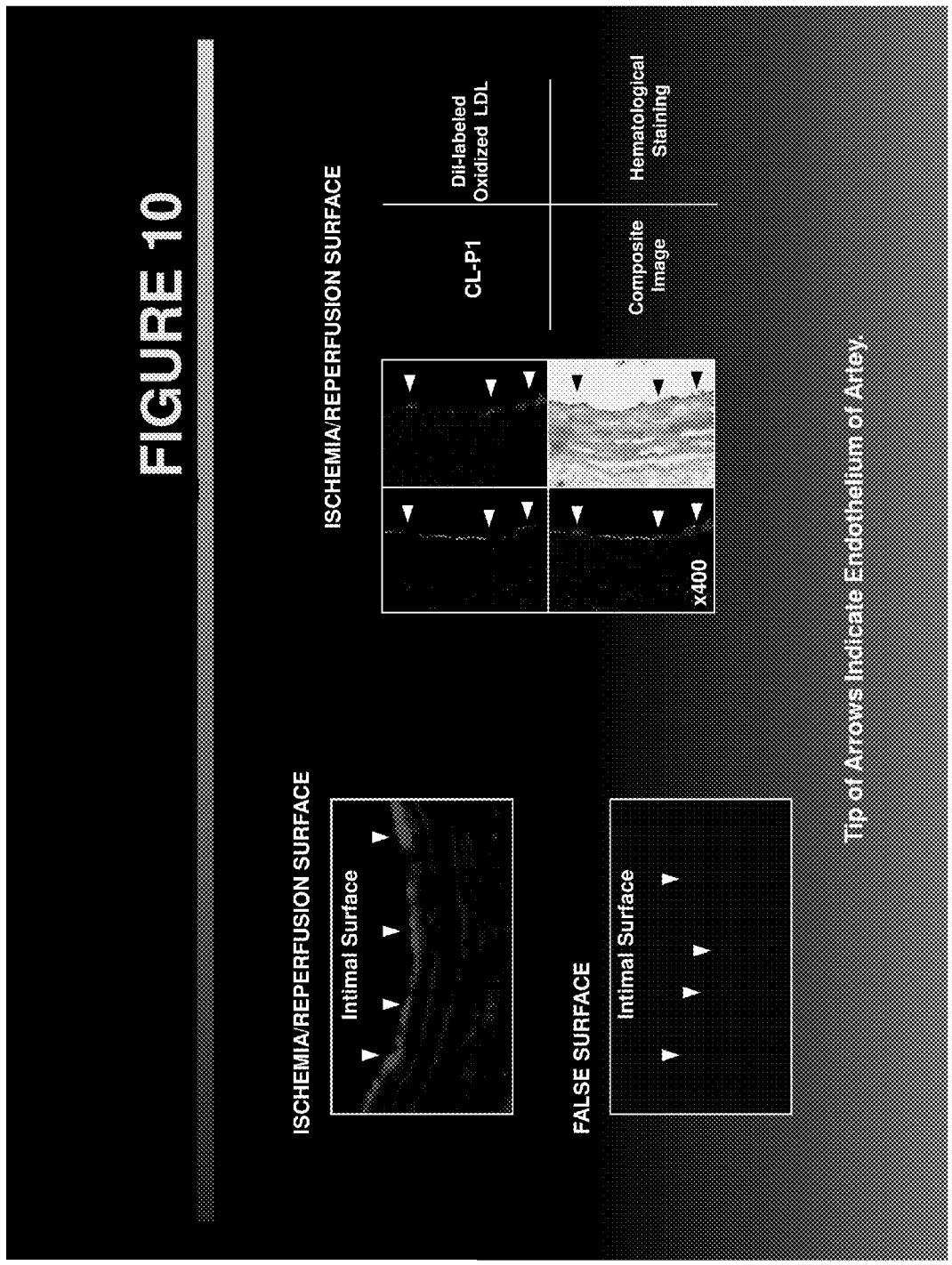

POLYPEPTIDE ACTING TO ENHANCE ISCHEMIC DISEASES

This application is a U.S. National Phase Application of International Applicantion No. PCT/JP2011/001285 filed Mar. 4, 2011, which in turn claims the benefit of priority of Japanese Patent Application No. 2010-047335 filed Mar. 4, 2010. The contents of all priority applications are incorporated herein by reference in their entirety.

TECHNICAL FIELD

The present invention relates to a polypeptide that plays a role in the mechanism of onset of ischemic disorder and that is particularly useful in the development of reagents and drugs favorable for use in the prevention and treatment of arteriosclerosis.

PRIOR ART

When the number of deaths in Japan today is analyzed by cause, the percentage of deaths associated with angiopathy is of course high and virtually rivals the number of cancer deaths. The majority of the cases of angiopathy are cases of disease in which arteriosclerosis plays a direct or an indirect role. The most common "arteriosclerotic disease" accompanied by hardening of the arteries is angiopathy in the form of aortic insufficiency, renal hypertension, ischemic heart disease, stroke, arteriosclerosis obliterans, and acute arterial obstruction.

Progression of arteriosclerosis eventually leads to collapse of vascular walls and vascular obstruction. According to the research conducted thus far, the morbid state of arteriosclerosis progresses due to dysfunction of endothelial cells; lipid deposition on the inside walls of the vessels and the resulting uptake of monocytic inflammatory cells to the vessel walls; differentiation and activation of these monocytic inflammatory cells as phagocytes; oxidative and enzymatic modification of the lipids inside the vessels, induction of local inflammation, and as a result, development of a variety of inflammatory reactions; and over-repair or anomalous repair accompanied by proliferation of smooth muscles at the vessel walls. That is, it appears that specific inflammatory and tissue repair reactions also participate in the morbid state of arteriosclerosis. For years we have stressed the importance of treating and managing factors involved in the onset of arteriosclerosis, such as hypertension, diabetes, hyperlipidemia, obesity, and smoking, in the prevention of progression of the disease.

DISCLOSURE OF INVENTION

Problems to Be Solved By Invention

In this technical field there is of course a demand for fundamental preventive methods and therapeutic methods that will not only counter the individual factors that are involved in the onset of arteriosclerosis, but also are proactive in arresting the progression of arteriosclerosis.

Means for Solving Problems

The inventors performed in-depth research in the light of the problems of prior art and discovered means for effectively preventing progression of arteriosclerosis.

That is, when summarized, the present invention provides a polypeptide comprising the amino acid sequence set out in Sequence No. 1 as a part thereof, the expression level of which is increased in the blood vessels of mammals that have been removed from an ischemic state by reperfusion of blood. Preferably the polypeptide of the present invention consists of the amino acid sequence represented by Sequence No. 1.

Effect of Invention

The present invention helps explain the mechanism involved in the onset of ischemic disease, and provides a polypeptide that can be used to develop reagents and drugs that are favorable for use in the prevention and treatment of arteriosclerosis.

BRIEF DESCRIPTION OF DRAWINGS

FIG. 2 is the alignment of the amino acid sequence of the conventional collectin polypeptide and the polypeptide of the present invention.

FIG. 8 is a drawing showing polypeptide expression at the mRNA level in an ischemia/reperfusion model.

FIG. 9 is a drawing showing increased polypeptide expression in a low-oxygen exposure/reoxygenation model.

FIG. 10 is a drawing showing intracellular uptake at the site of polypeptide expression.

PREFERRED EMBODIMENTS OF THE INVENTION

Figure 1:
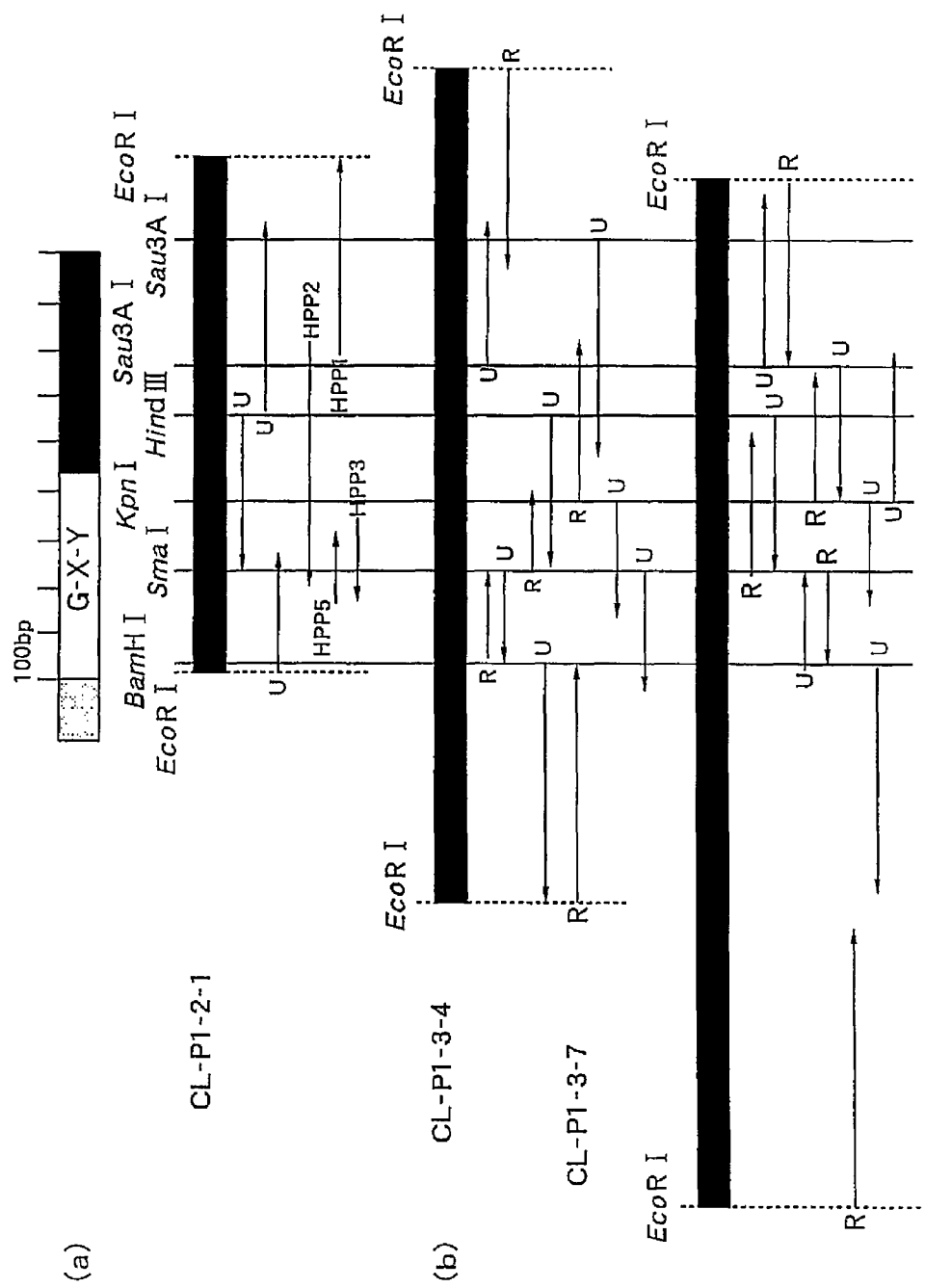
FIG. 1(a) is a drawing showing the open reading frame of the polypeptide of the present invention.
FIG. 1(b) is a drawing showing the base sequences specified as the names of the primers used in order to determine the base sequence of the polypeptide of the present invention.

Generally speaking, the polypeptide of the present invention is a protein belonging to the collectin family. A "collectin" is a protein having a calcium ion ($Ca^{2+}$)-requiring carbohydrate recognition domain (CRD) and collagen domain, and appears to participate in basic immunity in response to a variety of microorganisms, beginning with bacteria and viruses.

The collectins reported thus far are mannan-binding protein (MBP), surfactant protein A (SP-A), surfactant protein D (SP-D), and conglutinin. Of these, collectins such as conglutinin also participate in atypical immune response. For instance, there are reports that they play an important role in the neutralizing effect and elimination of a variety of microorganisms in children whose antibody transfer from the mother is incomplete and specific defense system is not fully developed (Super et al., Lancet, vol. 2, pp. 1236-1239 (1989)). Furthermore, there has also been research indicating that a host is easily infected when there is a reduction in the blood concentration of MBP as a result of a mutation on the MBP gene (Sumiya et al., Lancet, vol. 337, pp. 1569-1570 (1991)).

The inventors discovered that conglutinin and mannan-binding protein inhibit infection by types H1 and H3 influenza A virus and interfere with erythrocyte coagulation activity (Wakamiya et al., Glycoconjugate J. vol. 8, p. 235 (1991); Wakamiya et al., Biochem. Biophys. Res. Comm., vol. 187, pp. 1270-1278 (1992)). Thereafter, cDNA clones that encode conglutinin were acquired and a strong correlation between conglutinin and a variety of surfactant protein D genes was discovered (Suzuki et al., Biochem. Biophys. Res. Comm., vol. 191, pp. 335-342 (1993)).

As previously mentioned, the polypeptide of the present invention is characterized in that at least a portion thereof comprises the amino acid sequence represented by Sequence No. 1, and preferably consists of the amino acid sequence represented by Sequence No. 1.

In addition, the polypeptide of the present invention also includes the following six mutants substantially retaining the biological effect thereof:

Polypeptide mutant formed from an amino acid sequence (Sequence No. 2) wherein three amino acids are further bonded to the N terminus of the amino acid sequence in Sequence No. 1 that forms the polypeptide of the present invention, polypeptide mutant formed from an amino acid sequence (Sequence No. 3) wherein 18 amino acids are further bonded to the N terminus of the amino acid sequence in Sequence No. 1 that forms the polypeptide of the present invention, polypeptide mutant formed from an amino acid sequence (Sequence No. 4) wherein 127 amino acids are further bonded to the N terminus of the amino acid sequence in Sequence No. 1 that forms the polypeptide of the present invention, polypeptide mutant formed from an amino acid sequence (Sequence No. 5) wherein 138 amino acids are further bonded to the N terminus of the amino acid sequence in Sequence No. 1 that forms the polypeptide of the present invention, polypeptide mutant formed from an amino acid sequence (Sequence No. 6) wherein 220 amino acids are further bonded to the N terminus of the amino acid sequence in Sequence No. 1 that forms the polypeptide of the present invention, and polypeptide mutant formed from an amino acid sequence (Sequence No. 7) wherein 228 amino acids are further bonded to the N terminus of the amino acid sequence in Sequence No. 1 that forms the polypeptide of the present invention.

It should be noted that, as will be mentioned later, the polypeptide of the present invention is derived from humans, particularly from human placental tissue, and therefore, promises to have antibacterial activity and antiviral activity in humans in vivo and has the potential to be used as a biologically active pharmaceutical substance.

EXAMPLES

The present invention will be described using examples, but the present invention of course should not be restrictively interpreted on the basis of the disclosure in these examples.

Example 1

Screening of Human Placenta-Derived cDNA Library

First, the base sequence of the insert DNA of a fetal heart-derived clone (I.M.A.G.E. Consortium Clone ID 34472; GenBank/EST database Registration No. R74387) purchased from ATCC (American Type Culture Collection) was determined using M13 Universal Primer (Pharmacia, Sequence No. 8,5'-fluorescein-cgacgttgtaaaacgacggccagt-3') and M13 Lipase Primer (Pharmacia, Sequence No. 9,5'-fluorescein-caggaaacagctatgac-3').

A primer for digoxigenin (DIG)-labeled cDNA probe [reverse primer, acaatctgatgagaaggtgatg (Sequence No. 10) and forward primer, acgagggctggatgggacat (Sequence No. 11)] were prepared using the 392A DNA/RNA Synthesizer (Applied Biosystems). The DIG label was made using the PCR DIG Probe Synthesis Kit (Boehringer-Mannheim). The reaction composition is shown in the following Table 1.

TABLE 1

| Plasmid DNA (clone W72977, 500 ng/μL) | 2 μL (100 ng) |
| 10 × buffer | 5 μL |
| 25 mM MgCl$_2$ | 5 μL |
| dNTP (PCR labeling mix) | 5 μL |
| 20 reverse primer | 2.5 μL |
| 20 forward primer | 5 μL |
| Water | 28 μL |
| Taq polymerase | 0.5 μL |

The PCR reaction involved performing 35 times a cycle consisting of one minute at 92° C., one minute at 55° C., and two minutes at 72° C. using the Zymoreactor (Atto).

Next, titration of the human placenta-derived phage cDNA library was performed. That is, 0.2 mL of *Escherichia coli* Y1090r that had been cultured for 16 hours at 37° C. and 0.1 mL of cDNA library that had been serially diluted with SM buffer (5.8 g NaCl, 2 g MgSO$_4$.7H$_2$O, 25 mL of 2 M Tris-HCl (pH of 7.5), and 5 mL of 2% gelatin/L) were incubated for 15 minutes at 37° C. in an mLB medium (LB medium (1 g Trypton, 0.5 g yeast extract, 0.5 g NaCl/100 mL) containing 10 mM MgSO$_4$ and 0.2% of maltose). Then the product was added to 2.5 mL LB-top agaraose (0.75% agarose/LB medium) and homogenized and seeded in a 90 mm ø LB medium plate (Iwaki Garasu) (1.5% agar/LB medium). The product was allowed to harden for 15 minutes at room temperature and then incubated for five hours at 42° C. The plaques on each plate were counted and the phage titer was found by calculation. The titer was 2.1×10$^{10}$ pfu/mL.

Screening of these cDNA libraries was performed using the above-mentioned probe.

First, 0.6 mL of *Escherichia coli* Y1090r that had been cultured for 16 hours at 37° C. and 1×10$^5$ pfu of cDNA library diluted with SM buffer were incubated for 15 minutes at 37° C. in an mLB medium. Then 7.5 mL of LB-top agarose (0.75% agarose) was added and the product was homogenized. This was seeded into a 140 mm$^2$ LB medium square plate (Nissui Seiyaku). Ten of these plates were created. The plates were allowed to harden for 15 minutes at room temperature and then incubated for five hours at 42° C. Once plaque formation was confirmed, the plaques were transferred to a nylon membrane. Transfer was performed using the Nytran 13N (Schleicher and Schuell Co.). A 12.50 cm×9.0 cm filter was immersed in distilled water for ten minutes. Then the excess water was removed over Whatman 3 MM paper and the filter was placed over a plate that had formed plaques. Two minutes later, the filter was peeled away and the product was allowed to dry in air for ten minutes. The phage DNA was denatured for two minutes using 0.2 M NaOH/1.5M NaCl, neutralized for two minutes with 0.4 M Tris-HCl (pH 7.6)/2×SSC, and rinsed for two minutes with 2×SSC. Then the phage DNA was fixed on a membrane by UV exposure using a GS Gene Linker (Biorad).

Hybridization and signal detection were performed as described below.

First, a filter was moistened with 2×SSC and the excess water was removed with Whatman 3 MM paper. This filter was transferred to a hybridization bag and pre-hybridized at 68° C. together with hybridization solution (5×SSC, 1% blocking agent, 0.1% N-lauroylsarcosine, 0.02% SDS). Then the hybridization solution was removed from the hybridization bag and DIG-labeled cDNA probe was added to hybridization solution that had been brought to 10 ng/mL. Hybridization was performed for 16 hours at 55° C. Once hybridization was completed, the filter was rinsed twice for five minutes using 2×SSC/0.1% SDS solution at room temperature and then rinsed twice for 15 minutes with 0.5×SCC/0.1% SDS solution at 55° C. Next, the SDS was removed for 1 minute using DIG buffer I (100 mM Tris-HCl, 150 mM NaCl (pH 7.5)) and the filter was blocked for 30 minutes using DIG buffer II (1% blocking agent, DIG buffer I). The product was rinsed for one minute using DIG buffer and then a 1:5000 dilution of an anti-DIG alkaliphosphatase-labeled antibody (Boehringer-Mannheim) with DIG buffer was added and an antibody reaction was performed for 30 minutes at room temperature. The product was rinsed twice for 15 minutes with DIG buffer at room temperature. The magnesium ions ($Mg^{2+}$) concentration was raised by treatment for three minutes using DIG buffer III (100 mM Tris-HCl, 100 mM NaCl (pH 9.5), 50 mM $MgCl_2$). When the product was colored by a solution of NBT/BCIP (Wako Pure Chemical Industries) added to DIG buffer III, ten of the clones were positive. The plaques corresponding to these clones were cut from the plates, added to a tube containing 1 mL of SM buffer, stirred for ten minutes, and then serially diluted using SM buffer. 0.1 mL of this dilution and 0.2 mL of *Escherichia coli* Y1090r cultured for 16 hours at 37° C. in mLB medium were mixed and incubated for 15 minutes at 37° C. Then this mixture was added to 2.5 mL of LB-top agarose and homogenized. The product was seeded in a 90 mm ø LB medium plate. Ten of these plates were made. The plates were allowed to solidify for 15 minutes at room temperature and then incubated for five minutes at 42° C. Several plaques were thereby obtained and therefore, secondary screening was performed as with primary screening.

Example 2

Determination of Base Sequence of Selected Clone

Of the positive clones obtained by secondary screening, the plaques of clones considered appropriate were cut from the plate. These were added to a tube containing 200 µL of distilled water and stirred for 30 minutes at room temperature. The product was centrifuged for five minutes at 15,000 rpm to obtain a supernatant.

The resulting supernatant served as the template. Insert DNA was amplified by PCR using the TaKaRa LA PCR Kit ver. 2 (Takara Shuzo Co., Ltd.) The PCR reaction composition (brought to a total volume of 50 µL using water) is shown in the following Table 2.

TABLE 2

| Supernatant | 27 µL |
|---|---|
| 10 × LA PCR buffer II (magnesium ion-free) | 5 µL |
| 25 mM $MgCl_2$ | 5 µL |
| dNTP mix | 8 µL |
| 20 µM λgt11 reverse primer (sequence No.:) | 2.5 µL |
| 20 µM λgt11 reverse primer (sequence No.:) | 2.5 µL |
| LA Taq polymerase | 0.5 µL |
| Water | Balance |

The PCR reaction involved performing 30 cycles of 20 seconds at 98° C. and then five minutes at 68° C. using the GeneAmp PCR system 9600 (Applied Biosystems).

The PCR product was confirmed by 1% agarose gel electrophoresis and then purified by being cut from the gel. It should be noted that the Sephaglas B and Prep Kit (Pharmacia) was used for this purification.

The cut DNA fragment was incorporated in a pCR 2.1 vector of the TA Cloning Kit (Invitrogen). The TOP10F' cells contained in the TA Cloning Kit (Invitrogen) were transformed using a recombinant vector. The transformant was cultured in LB medium (100 µg/mL ampicillin) and three type of plasmid DNA were extracted for each clone by the alkali SDS method.

The resulting DNA was severed with the appropriate restriction enzyme and each DNA fragment was incorporated into a puC18 vector and transformed to XL-1 blue cells. The transformant was cultured in LB medium (100 µg/mL ampicillin) and the following plasmids were extracted by the alkali SDS method:

From CL-P1-2-1, plasmid containing EcoRI-HindIII fragment and HindIII-EcoRI fragment, from CL-P1-3-4, plasmid containing EcoRI-BamHI fragment, BamHI-SmaI fragment, SmaI-HindIII fragment, KpnI-Sau3A1 fragment, Sau3A1-EcoRI fragment, EcoRI-KPNI fragment, and EcoRI-SuraI fragment, and from CL-P1-3-7, EcoRI-BamHI fragment, BamHI-SmaI fragment, SmaI-HindIII fragment, KPn1-Sau3A1 fragment, Sau3A1-EcoRI fragment, EcoRI-KpnI fragment, and KpnI-EcoRI fragment.

The following primers were created using DNA/RNA synthesizer. The primers were labeled with the M13 Universal Primer (Sequence No. 8) and M13 Lipase Primer (Sequence No. 9) that came with the Autoread Sequencing Kit (Pharmacia), and FITC (Pharmacia fluoroprimer). The base sequence of the entire domain of these primers was determined using the Autoread Sequencing Kit (Pharmacia) and Autosequencer (ALF).

(Sequence No. 12)
HPP 1: 5'-Fluoresence'-cgtgaaaatgaatggaagtgg-3'

(Sequence No. 13)
HPP 2: 5'-Fluoresence-ttttatccattgctgttcctc-3'

(Sequence No. 14)
HPP 3: 5'-Fluoresence-ctggcagtccccgaggtccag-3'

(Sequence No. 15)
HPP 5: 5'-Fluoresence'-gctggtcccccggagagcgt-3'

FIG. 1 is a rough outline of determination of the base sequence.

FIG. 1(*a*) shows the open-reading frame (ORF) of the resulting polypeptide of the present invention, and the G-X-Y represents the collagen-like domain. FIG. 1(*b*) gives the name of each primer and shows the determined base sequence (with arrows). Similarly, it also shows the M13 universal Primer ("U" in the drawing) and M13 reverse primary ("R" in the drawing).

The base sequence of the 5' terminus region, which includes the transfer starting point of this sequence, was determined using the cDNA of the Cap portion.

A first PCR was performed using the Cap portion cDNA, 1RC2 primer (5'-caaggtacgccacagcgtatg-3' (sequence No. 16) that came with human liver (NIPPON GENE) and TGP1 primer (5'-tcttcagtttccctaatccc-3') (Sequence No. 17) synthesized by the Applied Biosystems 392A DNA/RNA synthesizer.

The reaction mixture (total volume of 50 µL) contained the composition shown in the following Table 3.

TABLE 3

LA PCR buffer II (magnesium ion-free)
2.5 mM MgCl$_2$
1 μL each of 200 μM dATP, dCTP, dGTP, and dTTP (Takara Shuzo Co., Ltd.)
cDNA human liver of Cap portion (NIPPON GENE)
0.5 μM 1RC2 primer (NIPPON GENE)
0.5 μM TGP1 primer PCR involved performing 35 cycles wherein one cycle consisted of denaturation at 95° C. for 20 seconds, annealing at 60° C. for 20 minutes, and extension at 72° C. for 20 seconds. Moreover, before the cycle process, a program of denaturing at 95° C. for five minutes and end with extension at 72° C. for 10 minutes was performed. Nested PCR was performed after the first PCR was completed.

Using 1 μL of the PCR product of the first PCRs the template, amplification was performed in accordance with the same reaction composition and program as in the first PCR (except that the number of cycles was 25) using the 2RC1 primer (5'-gtacgccacagcgtatgatgc-3' (Sequence No. 18)) that was provided and synthetic TGP2 primer (5'-cattcttgacaaact-tcatag-3' (Sequence No. 19)) (synthesized as with TGP1 primer).

The above-mentioned PCR reaction was performed using the TaKaRa PCR Thermal Cycler 480 (Takara Shuzo Co., Ltd.). The resulting PCR product was confirmed by agarose gel electrophoresis. Then the band was cut from the gel, frozen for ten minutes at −80° C., and centrifuged for ten minutes at 15,000 rpm. The supernatant was then purified by ethanol precipitation.

The purified DNA fragment was incorporated in the Novagen pT Blue Vector and this vector was transformed to competent cell XL 1-blue cells. The transformant was cultured in an LB medium (100 μg/mL ampicillin) and the plasmid was extracted by the alkali SDS method. The base sequence was determined using the AutoRead Sequencing Kit Pharmacia) and DNA Sequencer (A.L.F.). The M13 Universal Primer (Sequence No. 8) and the M13 Reverse Primer (Sequence No. 9) that came with the Autoread Sequencing Kit were used as the primers.

As a result, it could be confirmed that the cDNA clone acquired by Example 1 contained the 2,024 bases in Sequence No. 20 and had an open-reading frame of 1,026 bases. Moreover, it could be confirmed that a portion of this base sequence contained the domain that encodes the 319 amino acids in Sequence No. 1 (nucleotides at positions 739 through 1695 of the base sequence of Sequence No. 20).

Next, homology of the DNA and amino acid was searched using the GenBank data base, and as a result, the amino acid sequence that was obtained was obviously the sequence of a novel protein different from any of the previously discovered collectins.

Moreover, the amino acid sequence of three types of previously reported collectins and the amino acid sequence of the polypeptide of the present invention were compared. FIG. 2 shows the alignment. The area circled in black shows the homologous amino acid residue portions. These alignments show that the resulting polypeptide is homologous with conventional collectins and belongs to the collectin family.

Vector that can be Used in Present Invention

In addition to the vectors used in this example, an oligonucleotide encoding expression of the polypeptide of the present invention or an active fragment thereof can be used as long as it is a vector that allows for the expression of the polypeptide of the present invention.

In other words, it is possible to use any vector with which the polypeptide of the present invention can be replicated and expressed when the above-mentioned polynucleotide is incorporated in a replicon, such as a plasmid, λ phage, or cosmid.

Examples of vectors capable of being used to clone DNA fragment having longer chains than a cosmid are P1 phage, F factor, and yeast artificial pigment YAC. Moreover, the λ phage includes substitution-type vectors and insertion-type vectors, and these can be selected as needed in accordance with the length of the gene that is introduced.

Moreover, examples of vectors capable of being expressed in animal cells are SV40 vector, bovine papilloma virus vector, herpes virus vector, adenovirus vector, pox virus vector, and retrovirus vector. There are commercially available vectors, including pUC19 and pTV118N (Takara Shuzo Co., Ltd.), pUEX2 (Amersham), pGEX-4T and pKK233-2 (Pharmacia), pMAM-neo (Clontech), pGL2 (Promega) and pDNA3.1+ (Invitrogen). There are no special restrictions to the method for constructing these vectors, and they can be constructed using restriction enzyme, ligase, and the like by conventional methods known in this technological field.

Vectors that use bacteria, particularly *Escherichia coli*, as the host cell for transformation or transfection using the above-mentioned vector usually are formed from at least a promoter domain (including a promoter, operator, and Shine-Dalgrano sequence), start codon, base sequence encoding the polypeptide of the present invention, end codon, and terminator domain. The vector when yeast or animal cells are used as the host is preferably one that contains at least a promoter, start codon, signal peptide, base sequence encoding the polypeptide of the present invention, and end codon. Moreover, it is also possible to insert an enhancer sequence, the 5' and 3'-untranslated regions of the polypeptide of the present invention, splicing link, polyadenylation portion, and selection marker into the vector.

Examples of promoters that can be incorporated in the vector of the present invention are SV40 (Similian Virus 40), SRα, cytomegalovirus (CMV) promoter, actin promoter, viral LTR (Long Terminal Repeat), such as HTLV-1 LTR, HIV-LTR, and viral granuloma virus LTR, and herpes simplex tyrosine kinase virus promoter.

Moreover, cytometaglovirus, thymidine kinase (TK), β-actin, and SV40 early gene promoter are examples of conventional promoters for expression of many cell types, ranging from normal eukaryotes, such as fibroblasts, neurocytes, blood cells, or parenchyma cells, to cancer cells.

An enhancer is usually part of the promoter sequence and therefore can be used without further treatment.

It is also possible to select a promoter specific for the cell in question when a specific cell or tissue is to be expressed by introduction of a gene. Furthermore, there are cases in which the use of a homo-combination or hetero-combination of these promoters can be effective in that high expression can be expected and the polypeptide of the present invention is obtained with stability.

On the other hand, examples of promoters used for prokaryotic cells are PBAD, PL, trc, T7, SP6, TC, and lac. As long as they are compatible with the host, any promoter capable of high-level expression of the polypeptide of the present invention in cells derived from these prokaryotic cells can be selected as needed as the promoter of the present invention.

Moreover, it is also possible to select a promoter specific for the cell in question when a specific cell or tissue is to be expressed by introduction of a gene.

There are cases in which the use of a homo-combination or hetero-combination of these promoters can be effective in that high expression can be expected and the polypeptide of the present invention is obtained with stability.

GAL1, AOX1, CUPI, and PGK are examples of the promoter used in yeast.

Dihydrofolic acid dehydrogenase ("DHFR" hereafter) gene (methotrexate-resistant gene) and neo gene (G418-resistant gene) are examples of selection markers for recovering only the desired vector by incorporation in these vectors. For instance, when DHFR gene-deficient CHO cells are used and the DHFR gene is used as the selection marker, it is possible to select using a thymidine-free medium. Moreover, it is also possible to raise the methotrexate concentration and select resistant cells in order to express the genes within the cells and obtain a cell strain that expresses at a higher level.

Example 3

Genomic Southern Analysis

Genomic Southern analysis was performed in order to determine whether the gene that encodes expression of the polypeptide acquired in Example 2 is a single copy or a multiple copy.

The equivalent of 4 µg of human genome DNA (Promega) derived from human blood was digested by (1) EcoRI, (2) XbaI, (3) HindIII, (4) PstI, (5) BgIII or (6) BamHI restriction enzyme and subjected to electrophoresis for three hours at 100 mA in 0.8% agarose gel. Once migration was completed, the product was transferred on a nylon membrane (Nytran 13N) to produce the membrane for analysis. Transfer was performed after electrophoresis by immersion of the gel after in 100 mL of 0.25 N HCl for ten minutes, rinsing three times with distilled water, then immersion twice for 15 minutes in 100 mL of denaturation liquid (1.5 M NaCl, 0.5 M NaOH), and immersion for 30 minutes in 100 mL of a neutralization liquid (0.5 M Tris-HCl, 3 M NaCl (pH of 6.8)) for depurination, denaturation, and neutralization. Then transfer was performed using a vacuum blotting system (Toyobo Engineering, VB-30). In this case, the membrane had been pretreated for five minutes with 2×SSCI and then for five minutes with 20×SSCI. The pad had been soaked in 20×SSC. After transfer, the protein was fixed by UV exposure.

The probe for hybridization in Southern analysis was DNA probe [gaagacaagt cttcacatct tgttttcata aacactagag aggaacagca atggataaaa aaacagatgg tagggagaga gagccactgg atc a ggcctca cagactcaga g (Sequence No. 23)] that had been DIG labeled using a portion of the open reading frame of the cDNA sequence obtained in Working Example 1 and primers [5'-gaagacaagtettcaactettg-3' (sequence No. 21)] and 5'-ctct-gagtctgtgaggccgatc-3' (sequence No. 22). The probes were boiled for ten minutes and then subjected to quenching in dry ice/ethanol for five minutes before hybridization.

First, the after transfer, the membrane was immersed for five minutes in 2×SSC and then prehybridization was performed for 30 minutes at 65° C. in 10 mL of ExpressHyb hybridization solution (Clontech). Next, the frozen probe was diluted to 10 ng/mL using ExpressHyb hybridization solution and hybridization was performed for an hour at 65° C. using 2 mL of this solution.

After hybridization, the membrane was rinsed twice while shaking with 2×SSC and 20 mL of 0.1% SDS solution for five minutes each at room temperature and then was rinsed twice while shaking with 0.2 SSC and 20 mL of 0.1% SDS solution at 65° C. for 15 minutes each. In order to remove the SDS, the membrane was rinsed twice for one minute at room temperature using 50 mL of DIG buffer I (100 mM Tris-HCl, 150 mM NaCl (pH 7.5)) and then was blocked for an hour at room temperature using 50 mL of DIG buffer II' (1.5% blocking agent and DIG buffer).

Next, the membrane was treated for 30 minutes using 10 mL of a 1:5,000 dilution of anti-DIG alkali phosphatase-labeled antibody with DIG buffer I containing 0.2% Tween 20, and then rinsed twice while shaking for 20 minutes at room temperature using 50 mL of DIG buffer I containing 0.2% of Tween 20. The product was immersed twice for three minutes at room temperature in 10 mL of DIG buffer and then transferred to a Hybribag and a 1:100 dilution of CSPD (registered trademark, Boehringer Mannheim, chemilluminescent substrate) with DIG buffer III was spread such that it covered the entire membrane and the membrane was exposed on instant film T612 (Polaroid).

Figure 3:
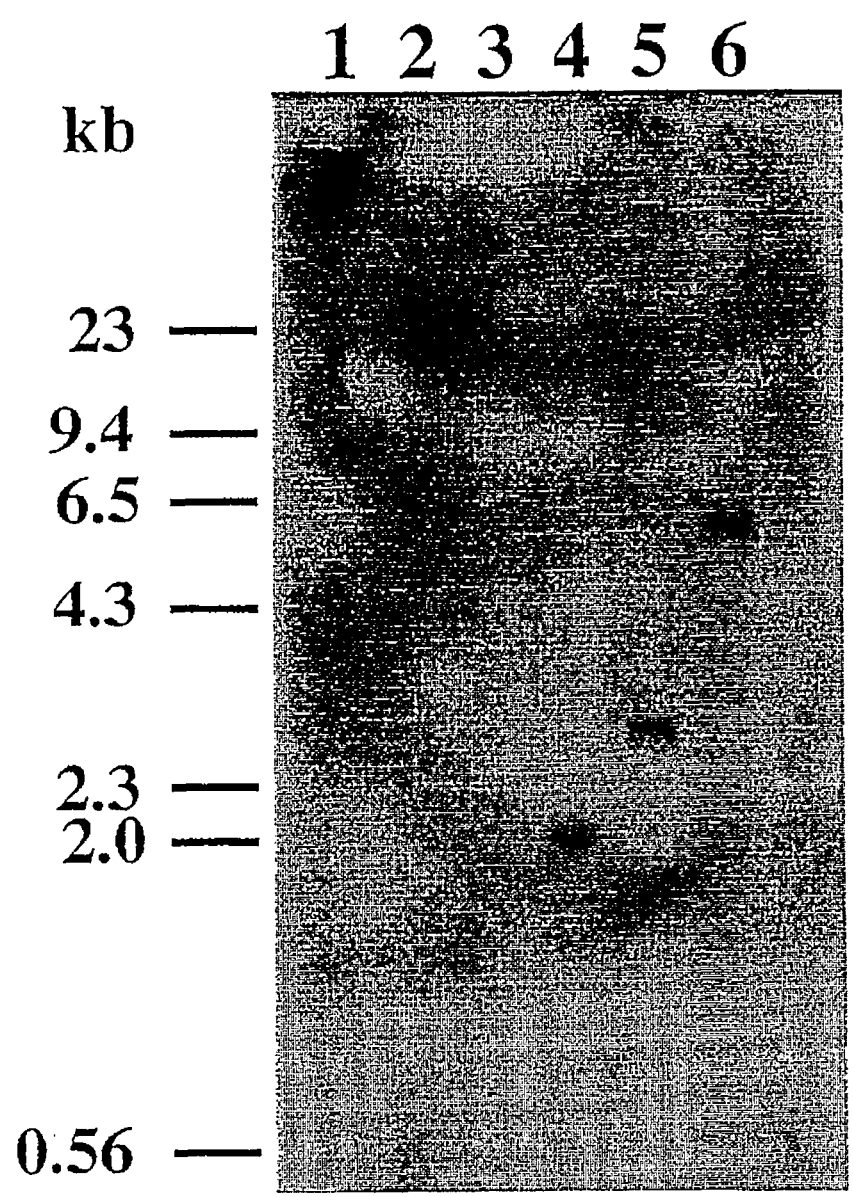
FIG. 3 is a drawing showing the results of genomic Southern analysis.

As a result, only one or two signals were detected from the genome DNA treated with each of the restriction enzymes, as shown by the respective lanes in FIG. 3. Therefore, the resulting genes that encode the polypeptide of the present invention were estimated to be single copy genes.

Example 4

Expression Distribution Analysis in Human Tissue

Expression in living tissue of the mRNA of the polypeptide of the present invention was analyzed by RT-PCR.

First, a variety of living tissues (organs) were prepared as described in the following Table 4. It should be noted that the colon tissue in lane 10 was purchased from Origene Technologies. RT-PCR was conducted using RNA LA PCR kit (AMV) Ver. 1.1 (Takara Shuzo Co., Ltd.), with the RNA derived from these living tissues as the template.

TABLE 4

| Lane No. (Figure 4) | Organ/tissue |
| --- | --- |
| 1 | Brain |
| 2 | Heart |
| 3 | Kidney |
| 4 | Spleen |
| 5 | Liver |
| 6 | Small intestine |
| 7 | Muscle tissue |
| 8 | Testis |
| 9 | Placenta |
| 10 | Colon |

First, a reverse transfer reaction was performed using the reaction composition shown in the following Table 5 (which was brought to a total volume of 20 µL using distilled water).

TABLE 5

| |
| --- |
| 5 mM MgCl$_2$ |
| 1 × RNA PCR buffer |
| 1 mM dNTP mixture |
| 1 U/µL RNase inhibitor |
| 0.25 U/µL reverse transcriptase |
| 0.125 µM oligo-dT-adapter primer |
| RNA 1 µg |
| RNase-free distilled water |

It should be noted that reverse-transcriptase-free reaction composition was prepared as the negative control.

The above-mentioned reaction solution was introduced to a 0.2 mL tube and PCR was performed for one cycle of 30 minutes at 42° C., five minutes at 99° C., and five minutes at 5° C. using the TaKaRa PCR Thermal Cycler PERSONAL (Takara Shuzo Co., Ltd.). The resulting PCR product was used to perform LA PCR of the reaction composition shown in Table 6.

TABLE 6

2.5 mM MgCl$_2$
1 × RNA PCR buffer II (magnesium ion-free)
2U TaKaRa LA Taq 0.2 μM of two types of primers (RT-PCR primer-U: 5'-gt-gcccctggccctgcagaatg-3' (Sequence No. 24) and RT-PCR primer-R: 5'-gcatatcaccctggggaacattttag-3' (Sequence No. 25) was added such that the carbohydrate recognition domain could be amplified from the next domain of the cDNA sequence of the resulting polypeptide and the product was brought to a volume of 80 μL using disinfected distilled water.

PCR involved performing one cycle of two minutes at 94° C. following be 50 cycles of 30 seconds at 94° C., 30 seconds at 60° C., and 1 minute and 30 seconds at 72° C. The reaction product was separated by 1% agarose gel electrophoresis and stained using ethidium bromide solution (0.1 μg/mL). The migration pattern was confirmed by using a transilluminator and the expressing tissue was identified.

Moreover, in order to compare the amount expressed by each tissue, RT-PCR was performed by amplifying a portion of the β-actin gene with each tissue and correcting the RNA. This method was performed by reverse transfer and PCR as described above and then evaluation using 1% agarose gel electrophoresis by the same technique as described above. The composition of the reverse transcriptase reaction (brought to a total volume of 60 μL using distilled water) was as shown in the following Table 7.

TABLE 7

5 mM MgCl$_2$
1 × RNA PCR buffer
1 mM dNTP mixture
1 U/μL RNase inhibitor
0.25 U/μL reverse transcriptase
2.5 μM random 9mer
RNA 10 ng
RNase-free distilled water PCR was performed for one cycle of ten minutes at 30° C., 15 minutes at 42° C., five minutes at 99° C., and five minutes at 5° C.

The resulting PCR product was used for PCR with the reaction composition in Table 8 (brought to a total volume of 40 μL using distilled water).

TABLE 8

2.5 mM MgCl$_2$
1 × LA PCR buffer II (magnesium ion-free)
2U TaKaRa LA taq
0.25 μM human β-actin sense primer (sequence No. 24)
0.25 μM human β-actin antisense primer (sequence No. 25)
Distilled water PCR involved performing 20 cycles of 15 seconds at 94° C. and 30 seconds at 68° C.

Figure 4:
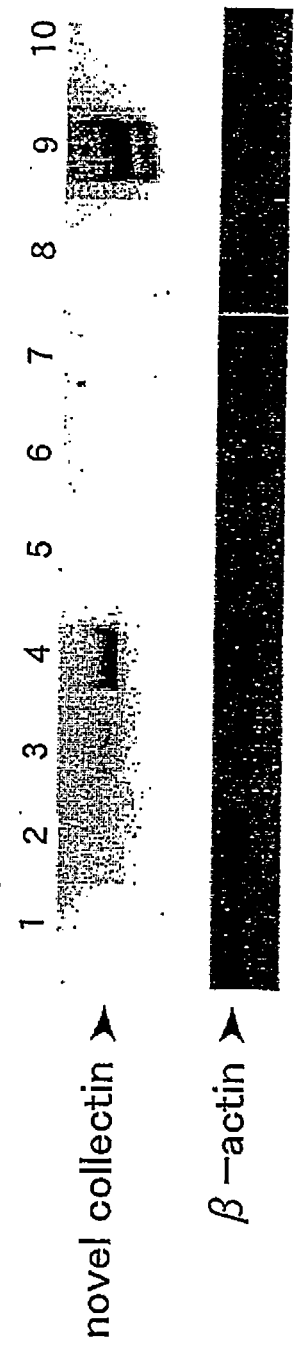
FIG. 4 is a drawing showing the tissue distribution of the polypeptide.

The results are shown in FIG. 4. The mRNA of the polypeptide of the present invention is obviously expressed in placenta (lane 9), the spleen (lane 4), and the kidneys (lane 3), but the expression level is particularly high in the placenta.

Example 5

Genomic Southern Analysis

Genomic Southern analysis was performed in order to ascertain whether the gene that encodes expression of the polypeptide of the present invention is conserved in animal species other than humans.

The probe for hybridization was a DNA probe obtained by labeling the portion corresponding to the above-mentioned open reading frame using the PCR DIG Probe Synthesis Kit (Boehringer-Mannheim). Moreover, the membrane was obtained by treating 5 μg of each genome DNA derived from the animals shown in the following Table 9 with restriction enzyme EcoRI, subjecting the product to electrophoresis with agarose gel, transferring the product on a Nytran 13N membrane, and fixing the transferred protein by exposure to UV rays.

TABLE 9

Figure 5:
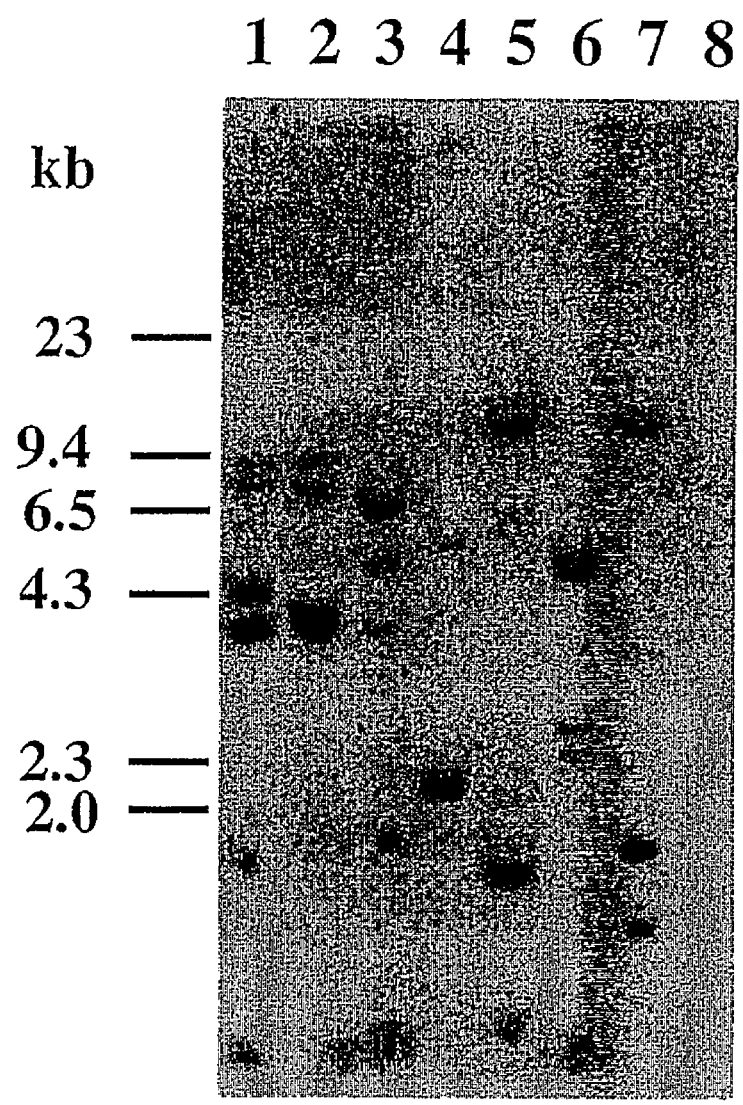
FIG. 5 is a drawing showing the conservation of the polypeptide between mammal species.

| Lane No. (Figure 5) | Species (source) |
| --- | --- |
| 1 | human (Promega) |
| 2 | monkey (Clontech) |
| 3 | rat (Promega) |
| 4 | mouse (Promega) |
| 5 | dog (Clontech) |
| 6 | cow (Promega) |
| 7 | rabbit (Clontech) |
| 8 | chicken (Promega) |

Hybridization was performed using the above-mentioned probe and membrane.

First, the membrane was immersed for five minutes in 2×SSC and then prehybridization was performed for 30 minutes at 65° C. in 10 mL of an ExpressHyb hybridization solution. The probe that had been similarly frozen was diluted to 10 ng/mL with Express Hyb hybridization solution and hybridization was performed for an hour at 65° C. using 2 mL of this solution.

After hybridization, the membrane was rinsed twice while shaking for five minutes at room temperature using 2×SSC and 20 mL of 0.1% SDS solution and then rinsed twice while shaking for 15 minutes at 68° C. using 0.2×SSC and 20 mL of 0.1% SDS solution. In order to remove the SDS, the membrane was further twice rinsed for one minute at room temperature using DIG buffer I and then blocking was performed for an hour at room temperature using 50 mL of DIG buffer II'.

Next, the membrane was treated for 30 minutes using 10 mL of a 1:5,000 dilution of anti-DIG alkali phosphatase-labeled antibody with DIG buffer containing 0.2% Tween 20. Then it was twice rinsed while shaking for 20 minutes at room temperature using 50 mL of DIG buffer I containing 0.2% of Tween 20. The product was immersed twice for three minutes at room temperature in 10 mL of DIG buffer III. The membrane was then transferred to a Hybribag and a 1:100 dilution of CSPD with DIG buffer was spread to cover the entire surface. The membrane was exposed on instant film T612.

Table 5 shows the results. A clear signal is observed in all animal species other than the chicken (Lane 8) in FIG. 5 and it is therefore obvious that the polypeptide gene of the invention is conserved in mammals.

Example 6

Genetic Analysis

Analysis was performed and a genetic genealogical tree (FIG. 6) was created in order to clarify the genetic position with conventional collectins on the basis of the structural DNA sequence of the gene that encodes expression of the polypeptide of the present invention.

Figure 6:
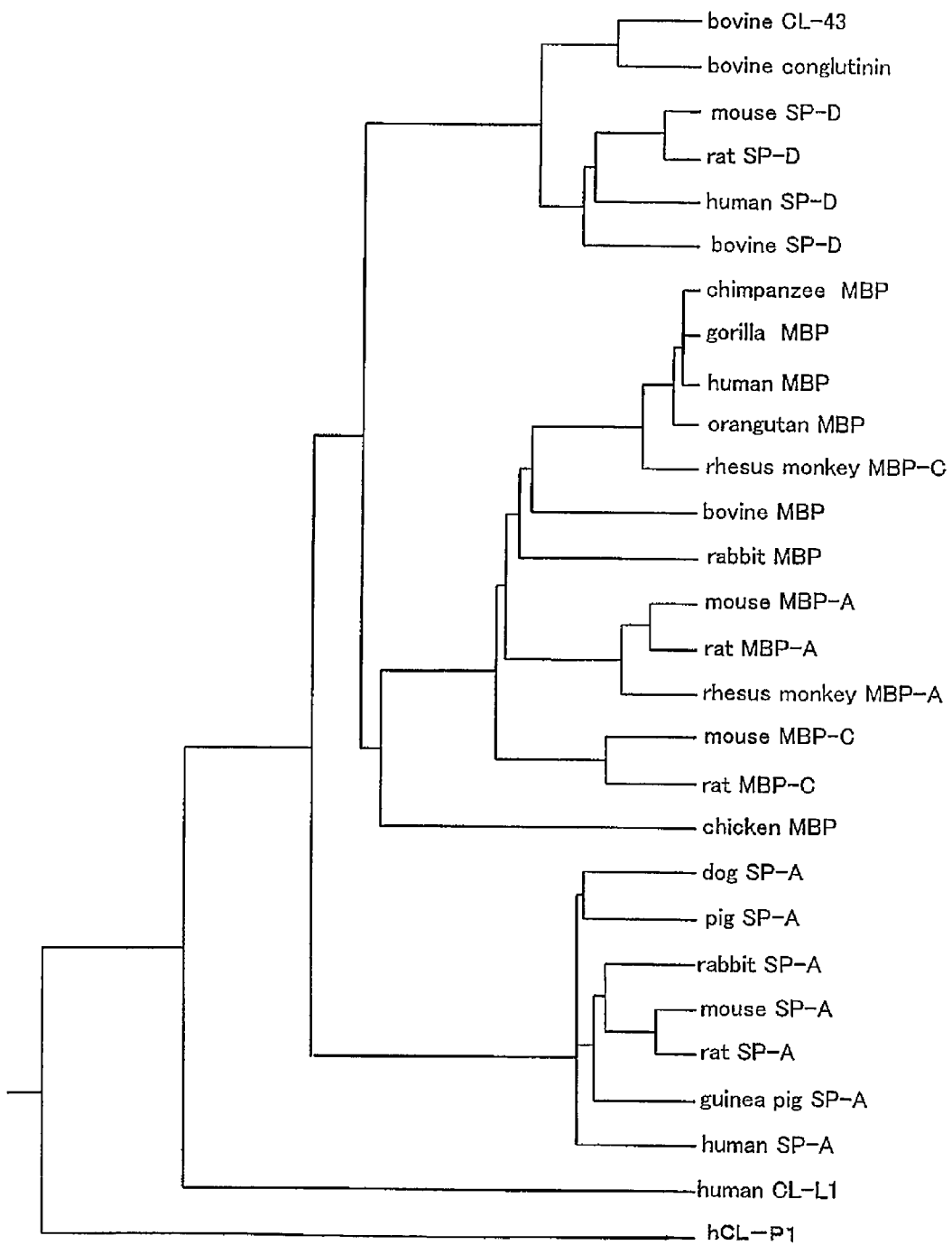
FIG. 6 is the genetic genealogy tree of collectin.

The collectin that is the subject of analysis is a protein of the collectin family shown in FIG. 6. The "CL-L1" in FIG. 6 is the human liver-derived collectin isolated by the inventors (refer to JP 11-206377).

Specifically, multiple alignments were created by the clustalw method using the domain including the lectin domain on the basis of the data obtained by probing each amino acid sequence from the GenBank data base. Moreover, on the basis of these alignments, a genetic tree was created using the NJ method (neighbor joining method) and the PHYLIP Version 3.57c package program.

Individual clusters were formed from SP-D, bovine CL-43, and bovine conglutinin and further, clusters were separately formed using MBP and SP-A. However, as with CL-L1, the gene encoding expression of the polypeptide of the present invention did not belong to any of the clusters. Moreover, the polypeptide of the present invention differed from CL-L1 in that it formed clusters that were genetically separate from the collectin previously reported.

Example 7

Expression Vector Construction

First, from the start codon to the end codon, the gene represented by the base sequence of Sequence No. 20 was amplified by the Zymoreactor (Atto) using primer formed from the base sequence aaggaaaaaa gcggccgcat gcaacaagat ttgatgagg (Sequence No. 26) and primer formed from the base sequence gctctagatt ataatgcaga tgacagtac (Sequence No. 27).

The resulting polypeptide cDNA was digested by restriction enzymes NotI and XbaI to acquire the portion corresponding to the cDNA of the polypeptide of the present invention (nucleotides at positions 670 to 1,698 of sequence No. 20) and this served as the insert.

Figure 7:
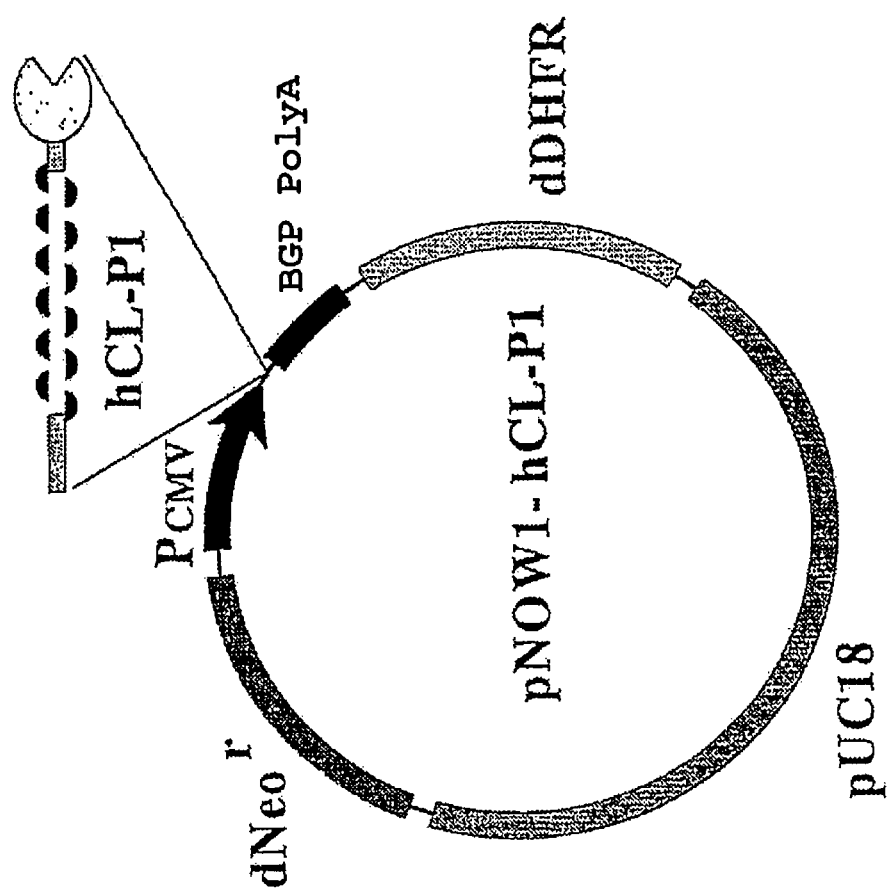
FIG. 7 is a schematic drawing showing the structure of the plasmid pNOW 1-hCL-P 1.

Next, expression vector pNOW/CMV-A described in JP (Kokai) 10-179169 was digested by restriction enzymes NotI and XbaI and the above-mentioned insert was inserted using a DNA ligation kit (Takara Shuzo Co., Ltd.) between PCMV (cytomegalovirus early main antigen promoter) and BGP polyA (bovine growth hormone polyadenylation signal). The expression vector obtained in this way is called plasmid pNOW1-hCL-P1 and FIG. 7 shows a schematic drawing of the structure of this vector.

Example 8

Selection of Produced Clones (1) Introduction of Plasmid pNOW 1-hCL-P1 into Host Cells Iscove's Modified Dulbecco's Medium (MDM) to which 10% of bovine fetal serum (FCS, GIBCO) had been added and medium free of hypoxanthine and thymidine (GIBCO) were prepared and DHFR gene-deficient (dhfr-) DG44 Chinese hamster ovarian (CHO) cell line was mixed with this to $1\times10^5$ cells/mL. This mixture was seeded in a dish having a diameter of 60 mm and cultured for 24 hours under conditions of 37° C. and 5% carbon dioxide gas ($CO_2$).

The culture supernatant was discarded and the volume was brought to 6 mL by adding separately prepared IMDM+10% FCS containing 100 μL of a solution obtained by mixing 5 μg DNA (plasmid pNOW 1-hCL-P1) with lipofectin solution (DOTAP liposome-type transfection reagent; Boehringer-Mannheim). Hypoxanthine (final concentration of 10 nM (GIBCO) and thymidine (final concentration of 100 nM) GIBCO) were added and the product was cultured for 16 hours in order to introduce plasmid pNOW 1-hCL-P1 to the dhfr-host CHO cells. Then the culture supernatant was discarded, 6 mL of IMDM to which 10% FCS, hypoxanthine, and thymidine had been added was mixed with the product, and the product was further cultured for 24 hours.

(2) Acquisition of Neomycin (G418)-Resistant CHO Cells

The cells to which the plasmid pNOW1-hCL-P1 had been introduced were cultured for 24 hours. The cells were treated with trypsin and recovered from the dish. After the number of cells was counted, the cells were suspended in 10% FCS+ IMDM containing neomycin (G418) at a concentration of 400 μg/mL such that there would be $1\times10^5$ cell/smL. ten 96-well microplates were inoculated (by injection) with the suspension at a rate of 0.1 mL/well. The product was cultured under conditions of 37° C. and 5% carbon dioxide gas ($CO_2$) and the cells that survived after two weeks served as the G418-resistant cells (clone).

These G418 resistant clones were confirmed to be capable of producing the polypeptide of the present invention.

Several of the clones confirmed to produce the polypeptide of the present invention were selected and a 25 $cm^2$ culture flask was inoculated with each of the clones. Culturing was performed until the cells were dense (until there were approximately $3\times10^6$ cells/25 $cm^2$ culture flask).

The culture supernatant of each culture flask was discarded and 2 mL of IMDM+10% FCS having the same composition as previously described was added. The cells were cultured for four days and then the culture supernatant was recovered.

The amount of polypeptide of the present invention (rhCL-P1: recombinant human polypeptide) produced that was contained in the recovered culture supernatant was determined.

It should be noted that the amount of polypeptide of the present invention that is produced is quantitatively determined in accordance with the method described in Y. Suzuki, et al., "Characterization of Recombinant Bovine Conglutinin Expressed in a Mammalian Cell," Biochem. Biophys. Res. Commun., vol 238, pp. 856-863 (1997). In concrete terms, the amount of polypeptide of the present invention that was produced was quantitatively determined according to the procedure in the same document using the polypeptide of the present invention expressed in *Escherichia coli* in accordance with the method of this document, anti-rabbit polyclonal antibody to the collectin carbohydrate recognition domain (CRD) and neck region (expressed by *Escherichia coli* using the same method), and the polypeptide of the present invention (quantitative determination subject).

(3) Acquisition of Methotrexate-Resistant CHO Cells

Once the clone that produced the polypeptide of the present invention that was obtained in Example 8(2) was subcultured and stabilized, a low concentration of methotrexate (MTX) was added to the medium and the gene was amplified.

First, each selected cell clone was added to IMDM+10% dialyzed FCS (JHR Bioscience) to which 5 nM MTX and 400 μg/mL of G418 had been added and ten 96-weel microplates were inoculated (by injection) with this mixture at a rate of 0.1 mL/well. Culturing was performed under conditions of 37° C. and 5% carbon dioxide gas ($CO_2$) and the cells that survived after two weeks were obtained as the 5 nM MTX-resistant cells (clone).

These 5 nM MTX-resistant clones are confirmed to produce the polypeptide of the present invention.

Several clones were arbitrarily selected from the clones confirmed to produce the polypeptide of the present invention, a 25 $cm^2$ culture flask was inoculated with each of the clones, and the clones were cultured for two weeks until the cells were dense. The supernatant was discarded and 2 mL of IMDM+10% FCS having the same composition as described above (with 5 nM MTX and 400 μg/mL of G418 added) was added. The product was cultured for four days, the culture supernatant was recovered, and the production level of the polypeptide of the present invention was confirmed.

(4) Quantitative Determination of Amount of Polypeptide of Present Invention Produced A solution of 100 μg of the polypeptide of the present invention dissolved in 100 μL of PBS (−) (PBS free of calcium and magnesium ions) and 100 μL of complete Freund's adjuvant were mixed and an emulsion was prepared. The emulsion was intraperitoneally injected in two BALB/c mice (female, 8-weeks-old).

Three weeks later, the mice were similarly immunized a second time. However, incomplete Freund's adjuvant was used in place of complete Freund's adjuvant.

Another two weeks later, serum was collected and the antibody titer was determined. The mouse with the highest titer was selected and one week later the final immunization was performed by the same method as the second immunization. Five days after the final immunization, the spleen was recovered and a cell suspension was prepared. Cell fusion was performed by mixing $2 \times 10^7$ NS-1 myeloma cells and $1 \times 10^8$ of the prepared pancreas cells. The mixture was centrifuged at 1,600 rpm and normal temperature for six minutes and the supernatant was removed. When the remaining cells had untangled, 1 mL of polyethylene glycol (PEG) was added over a one-minute period and then the mixture was stirred for a minute at room temperature. 1 mL of basic medium (Iscove's medium 15% FCS, 2 mM L-glutamine solution, 0.05 mM 2-mercaptoethanol) that had been kept at 37° C. was gently mixed while being added drop-wise over a one-minute period. After this procedure was repeated once, the same procedure was performed using 8 mL of medium added over a three-minute period. Then the product was centrifuged at 1,000 rpm and room temperature for five minutes in order to remove the PEG.

The pellets were untangled and 100 mL of a thymus cell suspension (suspended in hybridoma proliferating medium containing HAT, used as feeder cells for increasing hybridoma formation rate) was added at a rate of $5 \times 10^6$ cells/mL to prepare the suspension. This suspension was seeded 0.1 mL at a time in a 96-well plate and culturing was performed at 37° C. under 5% carbon dioxide in a carbon dioxide ($CO_2$) incubator.

The hybridoma was selected as follows.

Once day after culture was started, 150 μL of HAT medium (hybridoma proliferating medium containing HAT) was added to each well and then the product was cultured for two days. Two days later, 150 μL of the medium was removed and 150 μL of HAT medium was added as replacement medium. Medium replacement was performed after culturing for three days and seven days. Four days later, 100 μL of the culture supernatant was collected, the antibody titer to the polypeptide of the present invention was determined, and screening was performed. Next, the antibody-positive cells were transferred from the 96-well plate to a 24-well multiplate using a Pasteur pipette. 0.5 mL of HT medium (hybridoma proliferating medium containing hypoxanthine and thymidine) had been pre-added to each of the wells.

After culturing for three days, a portion of the medium was collected and the antibody titer was remeasured. The cells that were antibody-positive were cloned and freeze-dried. Cloning was performed by critical dilution of the positive cells with thymus cell suspension to 1 cell/mL and then seeding 0.1 mL at a time in a 96-well multiplate. After ten days of culturing, the antibody titer of the clones that formed one colony per well was measured and the two clones showing the highest antibody titers were selected.

Cloning was repeated using these two clones. The method was the same as for the first cloning. The antibody-positive cells were continuously cultured and magnified. First, the cells were transferred to a 24-well multiplate and culturing was performed for three days. Then the cells were transferred to a 25 cm² flask. Three days later, the cells were transferred to a 225 cm² flask, and culturing was continued for another three days. Then the culture supernatant was recovered to prepare the monoclonal antibody.

Moreover, monoclonal antibody was produced from ascites by preparation of cloned hybridoma to $1 \times 10^7$ cells/mL and then intraperitonal injection of 1 mL per mouse. Once week later, the mice with a swollen abdominal region were anesthetized with ether and the ascites was collected. The ascites was transferred to a coagulation-promoting centrifugation tube containing serum separator and after being set aside for 30 minutes at room temperature, was centrifuged for five minutes at 3,000 rpm. The top ascites was recovered and purified by ammonium sulfate precipitation to obtain antibody.

The resulting antibody (anti-mouse anti-human polypeptide antibody) was diluted to 10 μg/mL with coating buffer (50 mM carbonic acid-hydrogen carbonate buffer, pH 9.6) and this antibody solution was injected 100 μL at a time in a 96-well ELISA plate. Then the plate was incubated overnight at 4° C. The product was rinsed three times using 300 μL of rinsing solution (TBS/T solution (25 mM Tris-HCl, 0.14 M NaCl, 5 mM KCl, 0.05% Tween20, ph 7.4)). Subsequent rinsing was similarly performed. 300 μL of a 5% skin milk/TBS/T solution was injected and set aside for an hour at 37° C. After rinsing, 100 μL each of the polypeptide standard product of the present invention and sample reagent were injected into the plate and the plate was set aside for an hour at 37° C. After rinsing, 100 μL of 1 μg/mL biotinylated anti-rabbit anti-human polypeptide antibody was injected and the cell was set aside for 30 minutes at 37° C. After further rinsing, 100 μL of 3,3',5,5'-tetramethylbenzidine solution was injected and the product was set aside at room temperature for 30 minutes. 100 μL of 1 N phosphoric acid was added to stop the reaction and absorbance at a wavelength of 450 nm was measured.

An analysis curve was drawn from the standard product and the amount of polypeptide of the present invention that was produced was quantitatively determined.

Correlation Between Polypeptide and Mechanism of Onset of Ischemic Disease

Various problems such as activation of inflammatory cells, for instance, neutrophils, and production of active oxygen, locally occur with reperfusion of blood following a vascular ischemic disease such as myocardial infarction. An ischemia/reperfusion model using rats and mice is an example of an animal model that simulates such a condition, and this model is often used in research to ascertain the mechanism of these problems.

Therefore, tests on the dynamics of the polypeptide of the present invention after reperfusion of blood were performed using an ischemia/reperfusion model relating to the carotid artery of a rat.

First, the carotid artery of a rat (female, 8 weeks old) was brought to an ischemic state for 30 minutes and then expression of mRNA that participates in expression of the polypeptide of the present invention and expression of the same protein was examined over time during reperfusion of blood.

As a result, expression of the polypeptide of the present invention in the endothelium of the carotid artery was increased on the mRNA level after 48 hours, peaked after 72 hours, and then returned to the usual expression level after 120 hours, as shown in FIG. 8. Moreover, when the polypeptide of the present invention expressed in the vascular endothelial cells was observed on a protein level by immunostaining, expression was increased after three days, peaked on the seventh day, and was maintained even after 14 days. An increase of expression was not observed in the carotid artery of the opposite side (control) of the same individual that had not been subjected to ischemia/reperfusion.

Moreover, the same result was reported in a low-oxygen exposure/reoxygenation model using vascular endothelial cell HUFECs, which is an in vitro ischemia/reperfusion model relating to the carotid artery. That is, as is clear from the results in FIG. 9, increased expression was observed, even 72 hours after reoxygenation following 30 minutes of low-oxygen exposure.

The study findings indicated that the function of the polypeptide of the present invention is seen in the form of increased expression thereof, and the like when vascular stimulation, such as reperfusion, is applied after ischemia. Therefore, as is shown from the results in FIG. 10, when the dynamics of the polypeptide of the present invention were observed after adding a ligand such as denatured low-specific-gravity lipoprotein (denatured LDL) or oxygenated low-specific-gravity lipoprotein (oxidized LDL) at the time of increased expression, it is clear that binding and cellular uptake occur at the site of expression of the polypeptide of the present invention.

Therefore, the function of the polypeptide of the present invention is not displayed at a constant level, but when expression is induced locally by stimulation this function occurs upon the increase in expression. For instance, it is possible that the polypeptide of the present invention takes up oxidized LDL, which causes arteriosclerosis, and this leads to arteriosclerosis. In such a case, it may be possible to control this uptake and thereby prevent a variety of forms of angiopathy, beginning with arteriosclerosis, by administering the extracellular domain of the polypeptide of the present invention or the polypeptide of the domain that binds with the ligand thereof.

Industrial Applicability

The polypeptide of the present invention can be effectively used to help explain the mechanism of onset of ischemic disease, particularly disease leading to arteriosclerosis, and to develop reagents and drugs that are favorable for the prevention and treatment of these diseases.

The invention claimed is:

1. A method for treatment of angiopathy in a mammal comprising administering to the mammal a polypeptide consisting of the amino acid sequence of SEQ ID NO: 1.

2. The method of claim 1 wherein the angiopathy is arteriosclerosis.

* * * * *

SEQUENCE LISTING

```
<160> NUMBER OF SEQ ID NOS: 27

<210> SEQ ID NO 1
<211> LENGTH: 319
<212> TYPE: PRT
<213> ORGANISM: Homo Sapiens

<400> SEQUENCE: 1

Met Lys Leu Val Asp Ser Lys His Gly Gln Leu Ile Lys Asn Phe Thr
1               5                   10                  15

Ile Leu Gln Gly Pro Pro Gly Pro Arg Gly Pro Arg Gly Asp Arg Gly
            20                  25                  30

Ser Gln Gly Pro Pro Gly Pro Thr Gly Asn Lys Gly Gln Lys Gly Glu
        35                  40                  45

Lys Gly Glu Pro Gly Pro Pro Gly Pro Ala Gly Glu Arg Gly Pro Ile
    50                  55                  60

Gly Pro Ala Gly Pro Pro Gly Glu Arg Gly Gly Lys Gly Ser Lys Gly
65                  70                  75                  80

Ser Gln Gly Pro Lys Gly Ser Arg Gly Ser Pro Gly Lys Pro Gly Pro
                85                  90                  95

Gln Gly Pro Ser Gly Asp Pro Gly Pro Pro Gly Pro Pro Gly Lys Glu
            100                 105                 110

Gly Leu Pro Gly Pro Gln Gly Pro Pro Gly Phe Gln Gly Leu Gln Gly
        115                 120                 125

Thr Val Gly Glu Pro Gly Val Pro Gly Pro Arg Gly Leu Pro Gly Leu
130                 135                 140

Pro Gly Val Pro Gly Met Pro Gly Pro Lys Gly Pro Pro Gly Pro Pro
145                 150                 155                 160

Gly Pro Ser Gly Ala Val Val Pro Leu Ala Leu Gln Asn Glu Pro Thr
                165                 170                 175

Pro Ala Pro Glu Asp Asn Gly Cys Pro Pro His Trp Lys Asn Phe Thr
            180                 185                 190
```

```
Asp Lys Cys Tyr Tyr Phe Ser Val Glu Lys Glu Ile Phe Glu Asp Ala
        195                 200                 205
Lys Leu Phe Cys Glu Asp Lys Ser Ser His Leu Val Phe Ile Asn Thr
    210                 215                 220
Arg Glu Glu Gln Gln Trp Ile Lys Lys Gln Met Val Gly Arg Glu Ser
225                 230                 235                 240
His Trp Ile Gly Leu Thr Asp Ser Glu Arg Glu Asn Glu Trp Lys Trp
                245                 250                 255
Leu Asp Gly Thr Ser Pro Asp Tyr Lys Asn Trp Lys Ala Gly Gln Pro
            260                 265                 270
Asp Asn Trp Gly His Gly His Gly Pro Gly Glu Asp Cys Ala Gly Leu
                275                 280                 285
Ile Tyr Ala Gly Gln Trp Asn Asp Phe Gln Cys Glu Asp Val Asn Asn
        290                 295                 300
Phe Ile Cys Glu Lys Asp Arg Glu Thr Val Leu Ser Ser Ala Leu
305                 310                 315

<210> SEQ ID NO 2
<211> LENGTH: 322
<212> TYPE: PRT
<213> ORGANISM: Homo Sapiens

<400> SEQUENCE: 2

Met Glu Glu Met Lys Leu Val Asp Ser Lys His Gly Gln Leu Ile Lys
1               5                   10                  15
Asn Phe Thr Ile Leu Gln Gly Pro Pro Gly Pro Arg Gly Pro Arg Gly
            20                  25                  30
Asp Arg Gly Ser Gln Gly Pro Pro Gly Pro Thr Gly Asn Lys Gly Gln
        35                  40                  45
Lys Gly Glu Lys Gly Glu Pro Gly Pro Pro Gly Pro Ala Gly Glu Arg
    50                  55                  60
Gly Pro Ile Gly Pro Ala Gly Pro Pro Gly Glu Arg Gly Gly Lys Gly
65                  70                  75                  80
Ser Lys Gly Ser Gln Gly Pro Lys Gly Ser Arg Gly Ser Pro Gly Lys
                85                  90                  95
Pro Gly Pro Gln Gly Pro Ser Gly Asp Pro Gly Pro Pro Gly Pro Pro
            100                 105                 110
Gly Lys Glu Gly Leu Pro Gly Pro Gln Gly Pro Pro Gly Phe Gln Gly
        115                 120                 125
Leu Gln Gly Thr Val Gly Glu Pro Gly Val Pro Gly Pro Arg Gly Leu
    130                 135                 140
Pro Gly Leu Pro Gly Val Pro Gly Met Pro Gly Pro Lys Gly Pro Pro
145                 150                 155                 160
Gly Pro Pro Gly Pro Ser Gly Ala Val Val Pro Leu Ala Leu Gln Asn
                165                 170                 175
Glu Pro Thr Pro Ala Pro Glu Asp Asn Gly Cys Pro Pro His Trp Lys
            180                 185                 190
Asn Phe Thr Asp Lys Cys Tyr Tyr Phe Ser Val Glu Lys Glu Ile Phe
        195                 200                 205
Glu Asp Ala Lys Leu Phe Cys Glu Asp Lys Ser Ser His Leu Val Phe
    210                 215                 220
Ile Asn Thr Arg Glu Glu Gln Gln Trp Ile Lys Lys Gln Met Val Gly
225                 230                 235                 240
Arg Glu Ser His Trp Ile Gly Leu Thr Asp Ser Glu Arg Glu Asn Glu
                245                 250                 255
```

```
Trp Lys Trp Leu Asp Gly Thr Ser Pro Asp Tyr Lys Asn Trp Lys Ala
            260                 265                 270

Gly Gln Pro Asp Asn Trp Gly His Gly His Gly Pro Gly Glu Asp Cys
                275                 280                 285

Ala Gly Leu Ile Tyr Ala Gly Gln Trp Asn Asp Phe Gln Cys Glu Asp
    290                 295                 300

Val Asn Asn Phe Ile Cys Glu Lys Asp Arg Glu Thr Val Leu Ser Ser
305                 310                 315                 320

Ala Leu

<210> SEQ ID NO 3
<211> LENGTH: 337
<212> TYPE: PRT
<213> ORGANISM: Homo Sapiens

<400> SEQUENCE: 3

Met Arg Ser Arg Leu Asp Thr Glu Val Ala Asn Leu Ser Val Ile Met
1               5                   10                  15

Glu Glu Met Lys Leu Val Asp Ser Lys His Gly Gln Leu Ile Lys Asn
                20                  25                  30

Phe Thr Ile Leu Gln Gly Pro Pro Gly Pro Arg Gly Pro Arg Gly Asp
            35                  40                  45

Arg Gly Ser Gln Gly Pro Pro Gly Pro Thr Gly Asn Lys Gly Gln Lys
    50                  55                  60

Gly Glu Lys Gly Glu Pro Gly Pro Pro Gly Ala Gly Glu Arg Gly
65                  70                  75                  80

Pro Ile Gly Pro Ala Gly Pro Pro Gly Glu Arg Gly Gly Lys Gly Ser
                85                  90                  95

Lys Gly Ser Gln Gly Pro Lys Gly Ser Arg Gly Ser Pro Gly Lys Pro
            100                 105                 110

Gly Pro Gln Gly Pro Ser Gly Asp Pro Gly Pro Pro Gly Pro Pro Gly
        115                 120                 125

Lys Glu Gly Leu Pro Gly Pro Gln Gly Pro Pro Gly Phe Gln Gly Leu
130                 135                 140

Gln Gly Thr Val Gly Glu Pro Gly Val Pro Gly Pro Arg Gly Leu Pro
145                 150                 155                 160

Gly Leu Pro Gly Val Pro Gly Met Pro Gly Pro Lys Gly Pro Pro Gly
                165                 170                 175

Pro Pro Gly Pro Ser Gly Ala Val Val Pro Leu Ala Leu Gln Asn Glu
            180                 185                 190

Pro Thr Pro Ala Pro Glu Asp Asn Gly Cys Pro Pro His Trp Lys Asn
        195                 200                 205

Phe Thr Asp Lys Cys Tyr Tyr Phe Ser Val Glu Lys Glu Ile Phe Glu
    210                 215                 220

Asp Ala Lys Leu Phe Cys Glu Asp Lys Ser Ser His Leu Val Phe Ile
225                 230                 235                 240

Asn Thr Arg Glu Glu Gln Gln Trp Ile Lys Lys Gln Met Val Gly Arg
                245                 250                 255

Glu Ser His Trp Ile Gly Leu Thr Asp Ser Glu Arg Glu Asn Glu Trp
            260                 265                 270

Lys Trp Leu Asp Gly Thr Ser Pro Asp Tyr Lys Asn Trp Lys Ala Gly
        275                 280                 285

Gln Pro Asp Asn Trp Gly His Gly His Gly Pro Gly Glu Asp Cys Ala
    290                 295                 300
```

```
Gly Leu Ile Tyr Ala Gly Gln Trp Asn Asp Phe Gln Cys Glu Asp Val
305                 310                 315                 320

Asn Asn Phe Ile Cys Glu Lys Asp Arg Glu Thr Val Leu Ser Ser Ala
                325                 330                 335

Leu

<210> SEQ ID NO 4
<211> LENGTH: 446
<212> TYPE: PRT
<213> ORGANISM: Homo Sapiens

<400> SEQUENCE: 4

Met Glu Asn Ile Thr Thr Ile Ser Gln Ala Asn Glu Gln Asn Leu Lys
1               5                   10                  15

Asp Leu Gln Asp Leu His Lys Asp Ala Glu Asn Arg Thr Ala Ile Lys
                20                  25                  30

Phe Asn Gln Leu Glu Glu Arg Phe Gln Leu Phe Glu Thr Asp Ile Val
            35                  40                  45

Asn Ile Ile Ser Asn Ile Ser Tyr Thr Ala His His Leu Arg Thr Leu
        50                  55                  60

Thr Ser Asn Leu Asn Glu Val Arg Thr Thr Cys Thr Asp Thr Leu Thr
65                  70                  75                  80

Lys His Thr Asp Asp Leu Thr Ser Leu Asn Asn Thr Leu Ala Asn Ile
                85                  90                  95

Arg Leu Asp Ser Val Ser Leu Arg Met Gln Gln Asp Leu Met Arg Ser
                100                 105                 110

Arg Leu Asp Thr Glu Val Ala Asn Leu Ser Val Ile Met Glu Glu Met
            115                 120                 125

Lys Leu Val Asp Ser Lys His Gly Gln Leu Ile Lys Asn Phe Thr Ile
130                 135                 140

Leu Gln Gly Pro Pro Gly Pro Arg Gly Pro Arg Gly Asp Arg Gly Ser
145                 150                 155                 160

Gln Gly Pro Pro Gly Pro Thr Gly Asn Lys Gly Gln Lys Gly Glu Lys
                165                 170                 175

Gly Glu Pro Gly Pro Pro Gly Pro Ala Gly Glu Arg Gly Pro Ile Gly
                180                 185                 190

Pro Ala Gly Pro Pro Gly Glu Arg Gly Gly Lys Gly Ser Lys Gly Ser
            195                 200                 205

Gln Gly Pro Lys Gly Ser Arg Gly Ser Pro Gly Lys Pro Gly Pro Gln
210                 215                 220

Gly Pro Ser Gly Asp Pro Gly Pro Gly Pro Gly Lys Glu Gly
225                 230                 235                 240

Leu Pro Gly Pro Gln Gly Pro Pro Gly Phe Gln Gly Leu Gln Gly Thr
                245                 250                 255

Val Gly Glu Pro Gly Val Pro Gly Pro Arg Gly Leu Pro Gly Leu Pro
                260                 265                 270

Gly Val Pro Gly Met Pro Gly Pro Lys Gly Pro Pro Gly Pro Pro Gly
            275                 280                 285

Pro Ser Gly Ala Val Val Pro Leu Ala Leu Gln Asn Glu Pro Thr Pro
290                 295                 300

Ala Pro Glu Asp Asn Gly Cys Pro Pro His Trp Lys Asn Phe Thr Asp
305                 310                 315                 320

Lys Cys Tyr Tyr Phe Ser Val Glu Lys Glu Ile Phe Glu Asp Ala Lys
                325                 330                 335
```

-continued

```
Leu Phe Cys Glu Asp Lys Ser Ser His Leu Val Phe Ile Asn Thr Arg
            340                 345                 350

Glu Glu Gln Gln Trp Ile Lys Lys Gln Met Val Gly Arg Glu Ser His
            355                 360                 365

Trp Ile Gly Leu Thr Asp Ser Glu Arg Glu Asn Glu Trp Lys Trp Leu
            370                 375                 380

Asp Gly Thr Ser Pro Asp Tyr Lys Asn Trp Lys Ala Gly Gln Pro Asp
385                 390                 395                 400

Asn Trp Gly His Gly His Gly Pro Gly Glu Asp Cys Ala Gly Leu Ile
                    405                 410                 415

Tyr Ala Gly Gln Trp Asn Asp Phe Gln Cys Glu Asp Val Asn Asn Phe
            420                 425                 430

Ile Cys Glu Lys Asp Arg Glu Thr Val Leu Ser Ser Ala Leu
            435                 440                 445

<210> SEQ ID NO 5
<211> LENGTH: 457
<212> TYPE: PRT
<213> ORGANISM: Homo Sapiens

<400> SEQUENCE: 5

Met Asn Ser Gln Leu Asn Ser Phe Thr Gly Gln Met Glu Asn Ile Thr
1               5                   10                  15

Thr Ile Ser Gln Ala Asn Glu Gln Asn Leu Lys Asp Leu Gln Asp Leu
            20                  25                  30

His Lys Asp Ala Glu Asn Arg Thr Ala Ile Lys Phe Asn Gln Leu Glu
            35                  40                  45

Glu Arg Phe Gln Leu Phe Glu Thr Asp Ile Val Asn Ile Ile Ser Asn
    50                  55                  60

Ile Ser Tyr Thr Ala His His Leu Arg Thr Leu Thr Ser Asn Leu Asn
65                  70                  75                  80

Glu Val Arg Thr Thr Cys Thr Asp Thr Leu Lys His Thr Asp Asp
                85                  90                  95

Leu Thr Ser Leu Asn Asn Thr Leu Ala Asn Ile Arg Leu Asp Ser Val
            100                 105                 110

Ser Leu Arg Met Gln Gln Asp Leu Met Arg Ser Arg Leu Asp Thr Glu
            115                 120                 125

Val Ala Asn Leu Ser Val Ile Met Glu Glu Met Lys Leu Val Asp Ser
            130                 135                 140

Lys His Gly Gln Leu Ile Lys Asn Phe Thr Ile Leu Gln Gly Pro Pro
145                 150                 155                 160

Gly Pro Arg Gly Pro Arg Gly Asp Arg Gly Ser Gln Gly Pro Pro Gly
                165                 170                 175

Pro Thr Gly Asn Lys Gly Gln Lys Gly Glu Lys Gly Glu Pro Gly Pro
            180                 185                 190

Pro Gly Pro Ala Gly Glu Arg Gly Pro Ile Gly Pro Ala Gly Pro Pro
            195                 200                 205

Gly Glu Arg Gly Gly Lys Gly Ser Lys Gly Ser Gln Gly Pro Lys Gly
            210                 215                 220

Ser Arg Gly Ser Pro Gly Lys Pro Gly Pro Gly Pro Ser Gly Asp
225                 230                 235                 240

Pro Gly Pro Pro Gly Pro Pro Gly Lys Glu Gly Leu Pro Gly Pro Gln
                245                 250                 255

Gly Pro Pro Gly Phe Gln Gly Leu Gln Gly Thr Val Gly Glu Pro Gly
            260                 265                 270
```

-continued

```
Val Pro Gly Pro Arg Gly Leu Pro Gly Leu Pro Gly Val Pro Gly Met
        275                 280                 285

Pro Gly Pro Lys Gly Pro Gly Pro Pro Gly Pro Ser Gly Ala Val
    290                 295                 300

Val Pro Leu Ala Leu Gln Asn Glu Pro Thr Pro Ala Pro Glu Asp Asn
305                 310                 315                 320

Gly Cys Pro Pro His Trp Lys Asn Phe Thr Asp Lys Cys Tyr Tyr Phe
                325                 330                 335

Ser Val Glu Lys Glu Ile Phe Glu Asp Ala Lys Leu Phe Cys Glu Asp
                340                 345                 350

Lys Ser Ser His Leu Val Phe Ile Asn Thr Arg Glu Glu Gln Gln Trp
                355                 360                 365

Ile Lys Lys Gln Met Val Gly Arg Glu Ser His Trp Ile Gly Leu Thr
370                 375                 380

Asp Ser Glu Arg Glu Asn Glu Trp Lys Trp Leu Asp Gly Thr Ser Pro
385                 390                 395                 400

Asp Tyr Lys Asn Trp Lys Ala Gly Gln Pro Asp Asn Trp Gly His Gly
                405                 410                 415

His Gly Pro Gly Glu Asp Cys Ala Gly Leu Ile Tyr Ala Gly Gln Trp
                420                 425                 430

Asn Asp Phe Gln Cys Glu Asp Val Asn Asn Phe Ile Cys Glu Lys Asp
                435                 440                 445

Arg Glu Thr Val Leu Ser Ser Ala Leu
                450                 455

<210> SEQ ID NO 6
<211> LENGTH: 539
<212> TYPE: PRT
<213> ORGANISM: Homo Sapiens

<400> SEQUENCE: 6

Met Asn Leu Asn Asn Leu Asn Leu Thr Gln Val Gln Gln Arg Asn Leu
1               5                   10                  15

Ile Thr Asn Leu Gln Arg Ser Val Asp Asp Thr Ser Gln Ala Ile Gln
                20                  25                  30

Arg Ile Lys Asn Asp Phe Gln Asn Leu Gln Gln Val Phe Leu Gln Ala
            35                  40                  45

Lys Lys Asp Thr Asp Trp Leu Lys Glu Lys Val Gln Ser Leu Gln Thr
        50                  55                  60

Leu Ala Ala Asn Asn Ser Ala Leu Ala Lys Ala Asn Asn Asp Thr Leu
65                  70                  75                  80

Glu Asp Met Asn Ser Gln Leu Asn Ser Phe Thr Gly Gln Met Glu Asn
                85                  90                  95

Ile Thr Thr Ile Ser Gln Ala Asn Glu Gln Asn Leu Lys Asp Leu Gln
                100                 105                 110

Asp Leu His Lys Asp Ala Glu Asn Arg Thr Ala Ile Lys Phe Asn Gln
            115                 120                 125

Leu Glu Glu Arg Phe Gln Leu Phe Glu Thr Asp Ile Val Asn Ile Ile
        130                 135                 140

Ser Asn Ile Ser Tyr Thr Ala His His Leu Arg Thr Leu Thr Ser Asn
145                 150                 155                 160

Leu Asn Glu Val Arg Thr Thr Cys Thr Asp Thr Leu Thr Lys His Thr
                165                 170                 175

Asp Asp Leu Thr Ser Leu Asn Asn Thr Leu Ala Asn Ile Arg Leu Asp
                180                 185                 190
```

```
Ser Val Ser Leu Arg Met Gln Gln Asp Leu Met Arg Ser Arg Leu Asp
        195                 200                 205

Thr Glu Val Ala Asn Leu Ser Val Ile Met Glu Met Lys Leu Val
        210                 215                 220

Asp Ser Lys His Gly Gln Leu Ile Lys Asn Phe Thr Ile Leu Gln Gly
225                 230                 235                 240

Pro Pro Gly Pro Arg Gly Pro Arg Gly Asp Arg Gly Ser Gln Gly Pro
                245                 250                 255

Pro Gly Pro Thr Gly Asn Lys Gly Gln Lys Gly Glu Lys Gly Glu Pro
                260                 265                 270

Gly Pro Pro Gly Pro Ala Gly Glu Arg Gly Pro Ile Gly Pro Ala Gly
            275                 280                 285

Pro Pro Gly Glu Arg Gly Lys Gly Ser Lys Gly Ser Gln Gly Pro
        290                 295                 300

Lys Gly Ser Arg Gly Ser Pro Gly Lys Pro Gly Pro Gln Gly Pro Ser
305                 310                 315                 320

Gly Asp Pro Gly Pro Pro Gly Pro Gly Lys Glu Gly Leu Pro Gly
                325                 330                 335

Pro Gln Gly Pro Pro Gly Phe Gln Gly Leu Gln Gly Thr Val Gly Glu
        340                 345                 350

Pro Gly Val Pro Gly Pro Arg Gly Leu Pro Gly Leu Pro Gly Val Pro
            355                 360                 365

Gly Met Pro Gly Pro Lys Gly Pro Pro Gly Pro Pro Gly Pro Ser Gly
        370                 375                 380

Ala Val Val Pro Leu Ala Leu Gln Asn Glu Pro Thr Pro Ala Pro Glu
385                 390                 395                 400

Asp Asn Gly Cys Pro Pro His Trp Lys Asn Phe Thr Asp Lys Cys Tyr
                405                 410                 415

Tyr Phe Ser Val Glu Lys Glu Ile Phe Glu Asp Ala Lys Leu Phe Cys
                420                 425                 430

Glu Asp Lys Ser Ser His Leu Val Phe Ile Asn Thr Arg Glu Glu Gln
        435                 440                 445

Gln Trp Ile Lys Lys Gln Met Val Gly Arg Glu Ser His Trp Ile Gly
        450                 455                 460

Leu Thr Asp Ser Glu Arg Glu Asn Glu Trp Lys Trp Leu Asp Gly Thr
465                 470                 475                 480

Ser Pro Asp Tyr Lys Asn Trp Lys Ala Gly Gln Pro Asp Asn Trp Gly
                485                 490                 495

His Gly His Gly Pro Gly Glu Asp Cys Ala Gly Leu Ile Tyr Ala Gly
            500                 505                 510

Gln Trp Asn Asp Phe Gln Cys Glu Asp Val Asn Asn Phe Ile Cys Glu
        515                 520                 525

Lys Asp Arg Glu Thr Val Leu Ser Ser Ala Leu
530                 535

<210> SEQ ID NO 7
<211> LENGTH: 547
<212> TYPE: PRT
<213> ORGANISM: Homo Sapiens

<400> SEQUENCE: 7

Met Tyr Ser His Asn Val Val Ile Met Asn Leu Asn Asn Leu Asn Leu
1               5                   10                  15

Thr Gln Val Gln Gln Arg Asn Leu Ile Thr Asn Leu Gln Arg Ser Val
            20                  25                  30
```

-continued

```
Asp Asp Thr Ser Gln Ala Ile Gln Arg Ile Lys Asn Asp Phe Gln Asn
            35                  40                  45
Leu Gln Gln Val Phe Leu Gln Ala Lys Lys Asp Thr Asp Trp Leu Lys
 50                  55                  60
Glu Lys Val Gln Ser Leu Gln Thr Leu Ala Ala Asn Asn Ser Ala Leu
 65                  70                  75                  80
Ala Lys Ala Asn Asn Asp Thr Leu Glu Asp Met Asn Ser Gln Leu Asn
            85                  90                  95
Ser Phe Thr Gly Gln Met Glu Asn Ile Thr Thr Ile Ser Gln Ala Asn
            100                 105                 110
Glu Gln Asn Leu Lys Asp Leu Gln Asp Leu His Lys Ala Glu Asn
            115                 120                 125
Arg Thr Ala Ile Lys Phe Asn Gln Leu Glu Glu Arg Phe Gln Leu Phe
 130                 135                 140
Glu Thr Asp Ile Val Asn Ile Ser Asn Ile Ser Tyr Thr Ala His
 145                 150                 155                 160
His Leu Arg Thr Leu Thr Ser Asn Leu Asn Glu Val Arg Thr Thr Cys
            165                 170                 175
Thr Asp Thr Leu Thr Lys His Thr Asp Asp Leu Thr Ser Leu Asn Asn
            180                 185                 190
Thr Leu Ala Asn Ile Arg Leu Asp Ser Val Ser Leu Arg Met Gln Gln
 195                 200                 205
Asp Leu Met Arg Ser Arg Leu Asp Thr Glu Val Ala Asn Leu Ser Val
 210                 215                 220
Ile Met Glu Glu Met Lys Leu Val Asp Ser Lys His Gly Gln Leu Ile
 225                 230                 235                 240
Lys Asn Phe Thr Ile Leu Gln Gly Pro Pro Gly Pro Arg Gly Pro Arg
            245                 250                 255
Gly Asp Arg Gly Ser Gln Gly Pro Pro Gly Pro Thr Gly Asn Lys Gly
            260                 265                 270
Gln Lys Gly Glu Lys Gly Glu Pro Gly Pro Pro Gly Pro Ala Gly Glu
            275                 280                 285
Arg Gly Pro Ile Gly Pro Ala Gly Pro Pro Gly Glu Arg Gly Gly Lys
 290                 295                 300
Gly Ser Lys Gly Ser Gln Gly Pro Lys Gly Ser Arg Gly Ser Pro Gly
 305                 310                 315                 320
Lys Pro Gly Pro Gln Gly Pro Ser Gly Asp Pro Gly Pro Pro Gly Pro
            325                 330                 335
Pro Gly Lys Glu Gly Leu Pro Gly Pro Gln Gly Pro Pro Gly Phe Gln
            340                 345                 350
Gly Leu Gln Gly Thr Val Gly Glu Pro Gly Val Pro Gly Pro Arg Gly
            355                 360                 365
Leu Pro Gly Leu Pro Gly Val Pro Gly Met Pro Gly Pro Lys Gly Pro
 370                 375                 380
Pro Gly Pro Pro Gly Pro Ser Gly Ala Val Val Pro Leu Ala Leu Gln
 385                 390                 395                 400
Asn Glu Pro Thr Pro Ala Pro Glu Asp Asn Gly Cys Pro Pro His Trp
            405                 410                 415
Lys Asn Phe Thr Asp Lys Cys Tyr Tyr Phe Ser Val Glu Lys Glu Ile
            420                 425                 430
Phe Glu Asp Ala Lys Leu Phe Cys Glu Asp Lys Ser Ser His Leu Val
            435                 440                 445
Phe Ile Asn Thr Arg Glu Glu Gln Gln Trp Ile Lys Lys Gln Met Val
 450                 455                 460
```

```
Gly Arg Glu Ser His Trp Ile Gly Leu Thr Asp Ser Glu Arg Glu Asn
465                 470                 475                 480

Glu Trp Lys Trp Leu Asp Gly Thr Ser Pro Asp Tyr Lys Asn Trp Lys
                485                 490                 495

Ala Gly Gln Pro Asp Asn Trp Gly His Gly His Gly Pro Gly Glu Asp
            500                 505                 510

Cys Ala Gly Leu Ile Tyr Ala Gly Gln Trp Asn Asp Phe Gln Cys Glu
        515                 520                 525

Asp Val Asn Asn Phe Ile Cys Glu Lys Asp Arg Glu Thr Val Leu Ser
    530                 535                 540

Ser Ala Leu
545

<210> SEQ ID NO 8
<211> LENGTH: 24
<212> TYPE: DNA
<213> ORGANISM: Artificial Sequence
<220> FEATURE:
<223> OTHER INFORMATION: M13 Universal Primer

<400> SEQUENCE: 8
cgacgttgta aaacgacggc cagt                                        24

<210> SEQ ID NO 9
<211> LENGTH: 17
<212> TYPE: DNA
<213> ORGANISM: Artificial Sequence
<220> FEATURE:
<223> OTHER INFORMATION: M13 Reverse Primer

<400> SEQUENCE: 9
caggaaacag ctatgac                                                17

<210> SEQ ID NO 10
<211> LENGTH: 21
<212> TYPE: DNA
<213> ORGANISM: Artificial Sequence
<220> FEATURE:
<223> OTHER INFORMATION: Reverse Primer

<400> SEQUENCE: 10
caatctgatg agaaggtgat g                                           21

<210> SEQ ID NO 11
<211> LENGTH: 21
<212> TYPE: DNA
<213> ORGANISM: Artificial Sequence
<220> FEATURE:
<223> OTHER INFORMATION: Forward Primer

<400> SEQUENCE: 11
acgaggggct ggatgggaca t                                           21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
cgtgaaaatg aatggaagtg g                                           21
```

```
<210> SEQ ID NO 13
<211> LENGTH: 21
<212> TYPE: DNA
<213> ORGANISM: Artificial Sequence
<220> FEATURE:
<223> OTHER INFORMATION: Primer for Screening a Novel Collectin.

<400> SEQUENCE: 13
ttttatccat tgctgttcct c                                              21

<210> SEQ ID NO 14
<211> LENGTH: 21
<212> TYPE: DNA
<213> ORGANISM: Artificial Sequence
<220> FEATURE:
<223> OTHER INFORMATION: Primer for Sequencing a Novel Collectin.

<400> SEQUENCE: 14
ctggcagtcc ccgaggtcca g                                              21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gctggtcccc ccggagagcg t                                              21

<210> SEQ ID NO 16
<211> LENGTH: 21
<212> TYPE: DNA
<213> ORGANISM: Artificial Sequence
<220> FEATURE:
<223> OTHER INFORMATION: 1RC2 Primer

<400> SEQUENCE: 16
caaggtacgc cacagcgtat g                                              21

<210> SEQ ID NO 17
<211> LENGTH: 20
<212> TYPE: DNA
<213> ORGANISM: Artificial Sequence
<220> FEATURE:
<223> OTHER INFORMATION: TGP1 Primer

<400> SEQUENCE: 17
tcttcagttt ccctaatccc                                                20

<210> SEQ ID NO 18
<211> LENGTH: 21
<212> TYPE: DNA
<213> ORGANISM: Artificial Sequence
<220> FEATURE:
<223> OTHER INFORMATION: 2RC2 Primer

<400> SEQUENCE: 18
gtacgccaca gcgtatgatg c                                              21

<210> SEQ ID NO 19
<211> LENGTH: 21
<212> TYPE: DNA
<213> ORGANISM: Artificial Sequence
<220> FEATURE:
<223> OTHER INFORMATION: TGP2 Primer
```

-continued

<400> SEQUENCE: 19
cattcttgac aaacttcata g                                          21

<210> SEQ ID NO 20
<211> LENGTH: 2024
<212> TYPE: DNA
<213> ORGANISM: Homo Sapiens
<220> FEATURE:
<221> NAME/KEY: CDS
<222> LOCATION: (670)..(1695)

<400> SEQUENCE: 20
gtcacgaatc tgcagcaaga taccagcgtg ctccagggca atctgcagaa ccaaatgtat    60
tctcataatg tggtcatcat gaacctcaac aacctgaacc tgacccaggt gcagcagagg   120
aacctcatca cgaatctgca gcggtctgtg gatgacacag gccaggctat ccagcgaatc   180
aagaacgact ttcaaaatct gcagcaggtt tttcttcaag ccaagaagga cacggattgg   240
ctgaaggaga aagtgcagag cttgcagacg ctggctgcca caactctgc gttggccaaa    300 gccaacaacg acaccctgga ggatatgaac agccagctca actcattcac aggtcagatg   360
gagaacatca ccactatctc tcaagccaac gagcagaacc tgaaagacct gcaggactta   420
cacaaagatg cagagaatag aacagccatc aagttcaacc aactggagga acgcttccag   480
ctctttgaga cggatattgt gaacatcatt agcaatatca gttacacagc ccaccacctg   540
cggacgctga ccagcaatct aaatgaagtc aggaccactt gcacagatac ccttaccaaa   600
cacacagatg atctgacctc cttgaataat accctggcca catccgtttt ggattctgtt   660 tctctcagg atg caa caa gat ttg atg agg tcg agg tta gac act gaa gta    711
         Met Gln Gln Asp Leu Met Arg Ser Arg Leu Asp Thr Glu Val
           1               5                  10 gcc aac tta tca gtg att atg gaa gaa atg aag cta gta gac tcc aag     759
Ala Asn Leu Ser Val Ile Met Glu Glu Met Lys Leu Val Asp Ser Lys
 15               20                  25                  30 cat ggt cag ctc atc aag aat ttt aca ata cta caa ggt cca ccg ggc     807
His Gly Gln Leu Ile Lys Asn Phe Thr Ile Leu Gln Gly Pro Pro Gly
                 35                  40                  45 ccc agg ggt cca aga ggt gac aga gga tcc cag gga ccc cct ggc cca     855
Pro Arg Gly Pro Arg Gly Asp Arg Gly Ser Gln Gly Pro Pro Gly Pro
             50                  55                  60 act ggc aac aag gga cag aaa gga gag aag ggg gag cct gga cca cct     903
Thr Gly Asn Lys Gly Gln Lys Gly Glu Lys Gly Glu Pro Gly Pro Pro
 65                  70                  75 ggc cct gcg ggt gag aga ggc cca att gga cca gct ggt ccc ccc gga    951
Gly Pro Ala Gly Glu Arg Gly Pro Ile Gly Pro Ala Gly Pro Pro Gly
         80                  85                  90 gag cgt ggc ggc aaa gga tct aaa ggc tcc cag ggc ccc aaa ggc tcc    999
Glu Arg Gly Gly Lys Gly Ser Lys Gly Ser Gln Gly Pro Lys Gly Ser
 95                 100                 105                 110 cgt ggt tcc cct ggg aag ccc ggc cct cag ggc ccc agt ggg gac cca   1047
Arg Gly Ser Pro Gly Lys Pro Gly Pro Gln Gly Pro Ser Gly Asp Pro
                115                 120                 125 ggc ccc ccg ggc cca cca ggc aaa gag gga ctc ccc ggc cct cag ggc   1095
Gly Pro Pro Gly Pro Pro Gly Lys Glu Gly Leu Pro Gly Pro Gln Gly
            130                 135                 140 cct cct ggc ttc cag gga ctt cag ggc acc gtt ggg gag cct ggg gtg   1143
Pro Pro Gly Phe Gln Gly Leu Gln Gly Thr Val Gly Glu Pro Gly Val
        145                 150                 155 cct gga cct cgg gga ctg cca ggc ttg cct ggg gta cca ggc atg cca   1191
Pro Gly Pro Arg Gly Leu Pro Gly Leu Pro Gly Val Pro Gly Met Pro
    160                 165                 170

-continued

| | | |
|---|---|---|
| ggc ccc aag ggc ccc ccc ggc cct cct ggc cca tca gga gcg gtg gtg<br>Gly Pro Lys Gly Pro Pro Gly Pro Pro Gly Pro Ser Gly Ala Val Val<br>175                    180                      185                      190 | 1239 |
| ccc ctg gcc ctg cag aat gag cca acc ccg gca ccg gag gac aat ggc<br>Pro Leu Ala Leu Gln Asn Glu Pro Thr Pro Ala Pro Glu Asp Asn Gly<br>                    195                      200                      205 | 1287 |
| tgc ccg cct cac tgg aag aac ttc aca gac aaa tgc tac tat ttt tca<br>Cys Pro Pro His Trp Lys Asn Phe Thr Asp Lys Cys Tyr Tyr Phe Ser<br>              210                      215                      220 | 1335 |
| gtt gag aaa gaa att ttt gag gat gca aag ctt ttc tgt gaa gac aag<br>Val Glu Lys Glu Ile Phe Glu Asp Ala Lys Leu Phe Cys Glu Asp Lys<br>      225                      230                      235 | 1383 |
| tct tca cat ctt gtt ttc ata aac act aga gag gaa cag caa tgg ata<br>Ser Ser His Leu Val Phe Ile Asn Thr Arg Glu Glu Gln Gln Trp Ile<br>240                    245                      250 | 1431 |
| aaa aaa cag atg gta ggg aga gag agc cac tgg atc ggc ctc aca gac<br>Lys Lys Gln Met Val Gly Arg Glu Ser His Trp Ile Gly Leu Thr Asp<br>255                    260                      265                      270 | 1479 |
| tca gag cgt gaa aat gaa tgg aag tgg ctg gat gga aca tct cca gac<br>Ser Glu Arg Glu Asn Glu Trp Lys Trp Leu Asp Gly Thr Ser Pro Asp<br>                    275                      280                      285 | 1527 |
| tac aaa aat tgg aaa gct gga cag ccg gat aac tgg ggt cat ggc cat<br>Tyr Lys Asn Trp Lys Ala Gly Gln Pro Asp Asn Trp Gly His Gly His<br>      290                      295                      300 | 1575 |
| ggg cca gga gaa gac tgt gct ggg ttg att tat gct ggg cag tgg aac<br>Gly Pro Gly Glu Asp Cys Ala Gly Leu Ile Tyr Ala Gly Gln Trp Asn<br>305                    310                      315 | 1623 |
| gat ttc caa tgt gaa gac gtc aat aac ttc att tgc gaa aaa gac agg<br>Asp Phe Gln Cys Glu Asp Val Asn Asn Phe Ile Cys Glu Lys Asp Arg<br>          320                      325                      330 | 1671 |
| gag aca gta ctg tca tct gca tta taacggactg tgatgggatc acatgagcaa<br>Glu Thr Val Leu Ser Ser Ala Leu<br>335                    340 | 1725 |
| attttcagct ctcaaaggca aaggacactc ctttctaatt gcatcacctt ctcatcagat | 1785 |
| tgaaaaaaaa aaaagcactg aaaaccaatt actgaaaaaa aattgacagc tagtgttttt | 1845 |
| taccatccgt cattacccaa agacttggga actaaaatgt tccccagggt gatatgctga | 1905 |
| ttttcattgt gcacatggac tgaatcacat agattctcct ccgtcagtaa ccgtgcgatt | 1965 |
| atacaaatta tgtcttccaa agtatggaac actccaatca gaaaaggtt atcatcccg | 2024 |

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
gaagacaagt cttcaactct tg                                                                22

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
ctctgagtct gtgaggccga tc                                                               22

```
<210> SEQ ID NO 23
<211> LENGTH: 111
<212> TYPE: DNA
<213> ORGANISM: Artificial Sequence
<220> FEATURE:
<223> OTHER INFORMATION: Probe

<400> SEQUENCE: 23
gaagacaagt cttcacatct tgttttcata aacactagag aggaacagca atggataaaa      60
aaacagatgg tagggagaga gagccactgg atcggcctca cagactcaga g             111

<210> SEQ ID NO 24
<211> LENGTH: 22
<212> TYPE: DNA
<213> ORGANISM: Artificial Sequence
<220> FEATURE:
<223> OTHER INFORMATION: Forward Primer

<400> SEQUENCE: 24
gtgcccctgg ccctgcagaa tg                                              22

<210> SEQ ID NO 25
<211> LENGTH: 26
<212> TYPE: DNA
<213> ORGANISM: Artificial Sequence
<220> FEATURE:
<223> OTHER INFORMATION: Reverse Primer

<400> SEQUENCE: 25
gcatatcacc ctggggaaca ttttag                                          26

<210> SEQ ID NO 26
<211> LENGTH: 39
<212> TYPE: DNA
<213> ORGANISM: Artificial Sequence
<220> FEATURE:
<223> OTHER INFORMATION: Sense Primer

<400> SEQUENCE: 26
aaggaaaaaa gcggccgcat gcaacaagat ttgatgagg                            39

<210> SEQ ID NO 27
<211> LENGTH: 29
<212> TYPE: DNA
<213> ORGANISM: Artificial Sequence
<220> FEATURE:
<223> OTHER INFORMATION: Reverse Primer

<400> SEQUENCE: 27
gctctagatt ataatgcaga tgacagtac                                       29
```